(12) United States Patent
Moszner et al.

(10) Patent No.: US 7,605,190 B2
(45) Date of Patent: Oct. 20, 2009

(54) POLYMERIZABLE COMPOSITIONS WITH ACYLGERMANIUM COMPOUNDS

(75) Inventors: Norbert Moszner, Triesen (LI); Ulrich Salz, Lindau (DE); Urs Karl Fischer, Arbon (CH); Robert Liska, Vienna (AT); Heinrich Gruber, Vienna (AT); Beate Ganster, Vienna (AT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 11/902,865

(22) Filed: Sep. 26, 2007

(65) Prior Publication Data

US 2008/0277814 A1 Nov. 13, 2008

(30) Foreign Application Priority Data

Sep. 27, 2006 (EP) .................................. 06121333
Jul. 11, 2007 (EP) .................................. 07112299

(51) Int. Cl.
*A61C 13/00* (2006.01)
*A61C 13/225* (2006.01)
*A61K 6/00* (2006.01)
*C08F 2/50* (2006.01)
*C08J 3/28* (2006.01)

(52) U.S. Cl. ........................... 522/66; 522/33; 522/105; 522/109; 522/111; 522/113; 522/168; 522/173; 522/120; 522/121; 522/122; 522/134; 522/143; 522/144; 522/178; 522/182; 522/908; 523/105; 523/109; 523/111; 523/113; 523/115; 523/116; 523/117; 523/118; 523/120; 556/87

(58) Field of Classification Search ................... 522/33, 522/66, 168, 170, 113, 120, 121, 122, 134, 522/143, 144, 178, 182; 556/87; 523/105, 523/109, 111, 113, 114, 115, 116, 117, 118, 523/120

See application file for complete search history.

(56) References Cited

U.S. PATENT DOCUMENTS

| | | | |
|---|---|---|---|
| 3,887,650 A | 6/1975 | Agouri et al. | |
| 4,457,818 A | 7/1984 | Denyer et al. | |
| 4,525,256 A | 6/1985 | Martin | |
| 6,043,361 A | 3/2000 | Evans et al. | |
| 6,096,903 A | 8/2000 | Moszner et al. | |
| 6,344,556 B1 | 2/2002 | Evans et al. | |
| 6,511,317 B2 * | 1/2003 | Melikechi et al. | 433/29 |
| 2007/0287792 A1 * | 12/2007 | Moszner et al. | 524/556 |
| 2008/0076847 A1 | 3/2008 | Moszner et al. | |

FOREIGN PATENT DOCUMENTS

| | | |
|---|---|---|
| DE | 19616183 | 9/1997 |
| DE | 19903177 | 7/2000 |
| EP | 0405786 | 1/1991 |
| EP | 1247843 | 10/2002 |
| EP | 1413569 | 4/2004 |
| GB | 1408265 | 10/1975 |
| WO | WO9307230 | 4/1993 |
| WO | WO01/51533 | 7/2001 |
| WO | WO2005086911 | 9/2005 |

OTHER PUBLICATIONS

Diederishsen et al, "Biomolecular reactions of alkyl halides and acylgermanes: formation of ketones, diketones, and other products by radical-radical reaction", Journal of Organometallic Chemistry 531 (1997) 9-12.*

K. Yamamoto et al., "Preparation of Substituted Benzoyltrimethylsilanes and -germanes by the Reaction of Benzoyl Chlorides with Hexamethyldisilane or -digermane in the Presence of Palladium Complexes as Catalysts" Organometallics, 1987, vol. 6, pp. 974-979.

A. Castel et al., "New (Diarylgermyl) Lithiums", Organometallics, 1990, vol. 9, pp. 205-210.

T. Nishimura et al., "Synthesis of Acyltrialkylgermanes and Reactions with Carbon Nucleophiles" Chem. Soc. Perkin Trans., 1; 1994, pp. 1589-1595.

A.G. Brook et al., "Synthesis of Silyl and Germyl Ketones", J. Am. Chem. Soc. 1967, vol. 89, No. 1, pp. 431-434.

(Continued)

*Primary Examiner*—Sanza L McClendon
(74) *Attorney, Agent, or Firm*—Nixon Peabody LLP

(57) ABSTRACT

Composition with at least one polymerizable binder and at least one polymerization initiator, which contains at least one acylgermanium compound according to general Formula (I),

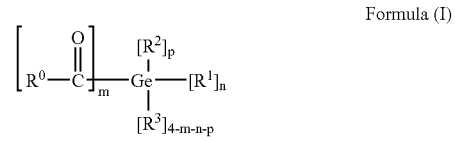

Formula (I)

in which $R^0$ is a substituted or unsubstituted $C_{1-18}$-alkyl radical or an acyl group; $R^1$ and $R^2$ are H, an acyl group or have one of the meanings given for $R^3$; $R^3$ is a branched or linear $C_{1-18}$-alkyl radical which can be unsubstituted or substituted one or more times by —O—, —NH—, —NR—, —S— or interrupted by other groups, trimethylsilyl, hal-$(CH_3)_2$Si—$[OSi(CH_3)_2]_r$—, $(CH_3)_3$Si—$[OSi(CH_3)_2]_r$—, —COOH, —COO—$R^{10}$, —CO—$NR^{11}R^{12}$, —CO-vinyl, —CO-phenyl, phenyl-$C_{1-4}$-alkyl, phenyl, naphthyl or biphenyl, $C_{5-12}$ cycloalkyl, a 5 or 6-membered O, S or N-containing heterocyclic ring, halogen, OH, an aromatic $C_{6-30}$ radical which can be substituted or unsubstituted and/or interrupted by O, S or —NR—, or a branched, cyclic or linear $C_{1-20}$ alkyl, -alkenyl, -alkoxy or -alkenoxy radical; m is 1, 2 or 3; n is 0 or 1 and p is 0 or 1; wherein in each case two of the radicals $R^0$, $R^1$, $R^2$ or $R^3$ can be connected to each other accompanied by the formulation of a 5 to 8 member ring; and the use of acylgermanium compounds of Formula (I), for example, as initiator for radical polymerization.

21 Claims, No Drawings

OTHER PUBLICATIONS

H.K. Sharma et al., "Organometalloidal Derivatives of the Transition Metals, XXVII, Chemical and Structural Investigations on (Ferrocenylacyl) Germanes", Journal of Organometallic Chemistry 1991, vol. 409, pp. 321-330.

J.P. Fouassier et al., "Radiation Curing in Polymer in Polymer Science and Technology—vol. II", Elsevier Applied Science, London and New York, 1993.

J.V. Crivello and Dr. K. Dietliker, "Photoinitiators for Free Radical Cationic & Anionic Photopolymerization," 2nd Ed. SITA Technology Ltd., London UK, 1998, pp. 228-239.

Extended European Search Report dated Aug. 22, 2008.

* cited by examiner

POLYMERIZABLE COMPOSITIONS WITH ACYLGERMANIUM COMPOUNDS

This application claims priority pursuant to 35 U.S.C. § 119, to European Patent Application No. 06121333.6 filed Sep. 27, 2006, and to European Patent Application No. 07112299.8 filed Jul. 11, 2007, the entire contents of which are incorporated herein by reference.

CROSS-REFERENCE TO RELATED APPLICATIONS

U.S. patent application Ser. No. 11/730,533, filed Apr. 2, 2007 is currently pending, is commonly owned, has at least one inventor in common with the present application, and has a priority date within two months of the priority date of the present application.

FIELD

The present invention relates to polymerizable compositions which contain an acylgermanium compound as a polymerization initiator. The compositions can be used for the preparation of adhesives, coatings, cements, composites, preshaped parts, and in particular dental materials.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art.

The initiator used plays a decisive role in the curing of polymerizable resins. Upon irradiation, photoinitiators absorb UV or visible light and form the polymerization-initiating species. In the event of radical polymerization these are free radicals. The photoinitiators are divided into two classes based on the chemical mechanism of radical formation.

Norrish type I photoinitiators form free radicals upon irradiation by unimolecular bond cleavage. Upon irradiation, Norrish type II photoinitiators undergo a bimolecular reaction wherein the excited photoinitiator reacts with a second molecule, the coinitiator, and forms the polymerization-initiating radicals by electron and proton transfer or direct hydrogen abstraction. Type I and type II photoinitiators are used for UV light curing; to date almost exclusively type II photoinitiators are used for the visible light range.

UV curing is characterized by a high reaction rate and is frequently used for the coatings of different substrates such as wood, metal or glass. Thus, for example, in EP 1 247 843 a UV curing coating material is described in which type I photoinitiators such as diethoxyphenylacetophenone or acylphosphine oxide are used.

WO 01/51533 describes a UV-curing wood-coating material in which acylphosphine oxides, α-hydroxyalkylphenones or α-dialkoxyacetophenones are likewise used as photoinitiators. Above all, transparent coatings with low layer thickness can be UV-cured due to the low wavelength of the UV light; however, the limit of UV curing is reached with pronounced shading or pigmentation and greater layer thicknesses. Such photopolyreactive resins cure only incompletely with UV light. Moreover, with pigmented compositions an absorption range must be found for the photoinitiator in which the pigment absorbs only weakly.

If greater through-curing depths are required, such as in the curing of light-curing dental filling materials, visible light is usually used for irradiation. The photoinitiator system most frequently used for this is a combination of an α-diketone with an amine coinitiator as is described in GB 1 408 265.

Dental compositions in which this photoinitiator system is used are disclosed in U.S. Pat. No. 4,457,818 or U.S. Pat. No. 4,525,256, wherein camphorquinone is preferably used an α-diketone. Camphorquinone has an absorption maximum at a wavelength of 468 nm. As a result camphorquinone displays a strong yellow coloring with the disadvantage that materials initiated with camphorquinone/amine have a noticeable yellow cast after curing. This is very disadvantageous in particular in the case of bright white shades of the fully polymerized material.

A further disadvantage of type II photoinitiators is that they lead to the formation of a sticky surface layer upon polymerization. This so-called inhibition layer is attributable to the inhibition of the radical polymerization by oxygen in air.

EP 0 405 786 A2 discloses initiators based on silicon, germanium or tin which are said to be suitable for the mass polymerization of acrylic monomers in an extruder. The initiators are used together with co-catalysts such as tetrabutylammonium fluoride. Silicon-based initiators such as 9-trimethylsilylcarbazole are preferred.

SUMMARY

One aspect of the invention is to provide polymerization initiators which can be activated by visible light and which result in a high through-curing depth of the material to be cured. The initiators are to be effective at low concentration and make possible a rapid curing of the material to be cured. Moreover, they are not to lead to discolorations of the material.

According to one aspect, the present invention provides a composition with at least one polymerizable binder and at least one polymerization initiator the composition comprising: at least one polymerizable binder and a polymerization initiator, the composition comprising at least one acylgermanium compound according to Formula (I),

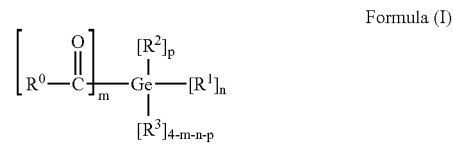

Formula (I)

in which $R^0$ is $C_{1-18}$ alkyl, $C_{2-18}$ alkenyl, wherein these radicals can be unsubstituted or substituted one or more times by halogen, $-OR^{10}$, $-OCO-R^{10}$, $-OCO$-hal, $-COO-R^{10}$, $-CH=CH-CO-OR^{10}$, $-N(R^{11})-CO-R^{10}$, $-N(R^{11})-CO$-hal, $-C(C_{1-4}$-alkyl$)=C(C_{1-4}$-alkyl$)-CO-OR^{10}$, $-CO-NR^{11}R^{12}$, $-CH=CH$-phenyl, $-C(C_{1-4}$-alkyl$)=C(C_{1-4}$-alkyl$)$ phenyl, $C_{3-12}$ cycloalkyl, $C_{2-18}$ alkenyl, phenyl-$C_{1-4}$-alkyl, phenyl, naphthyl, antryl, biphenyl, a saturated or unsaturated 5 or 6-membered O, S or N-containing heterocyclic ring, wherein said ring systems can be unsubstituted or substituted by 1 to 5 halogen atoms, $C_{1-8}$ alkyl, $C_{1-8}$ alkoxy and/or $C_{1-8}$ alkylthio radicals, or $R^0$ comprises:

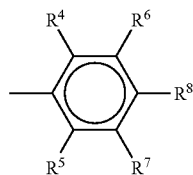

wherein
$R^4$, $R^5$ independently of each are H, halogen, a branched or linear $C_{1-6}$ alkyl or —O—$C_{1-6}$-alkyl radical which can be interrupted by one or more oxygen atoms;
$R^6$, $R^7$, $R^8$ independently of each other are H, halogen, a branched, cyclic or linear $C_{1-20}$ alkyl, -alkenyl, -alkyloxy or -alkenoxy radical, which can be interrupted by one or more O, S or —NR'— and can be substituted by one or more polymerizable groups and/or radicals $R^9$, wherein R' is H, halogen, a branched, cyclic or linear $C_{1-20}$ alkyl, -alkenyl, -alkyloxy or -alkenoxy radical;
wherein
$R^9$ is —OH, —$C_xF_{2x+1}$ with x=1 to 20, —[Si(CH$_3$)$_2$]$_y$—CH$_3$ with y=1 to 20;
$R^{10}$ is H; $C_{1-18}$ alkyl, $C_{1-18}$ alkyl which is interrupted by one or more oxygen atoms; $C_{2-18}$ alkenyl; $C_{2-18}$ alkenyl which is interrupted by one or more oxygen atoms; $C_{3-12}$ cycloalkyl; tetrahydropyran-2-yl, phenyl-$C_{1-20}$-alkylene; phenyl-$C_{1-20}$-alkenylene, $C_{1-6}$ alkyl which can be unsubstituted or substituted by halogen, cyclohexyl, cyclopentyl, tetrahydrofuranyl, furanyl or isopropyl-4-methyl-cyclohexyl, phenyl, naphthyl or biphenyl, wherein these ring systems can be unsubstituted or substituted by 1 to 5 halogen atoms, $C_{1-8}$-alkyl, $C_{1-8}$-alkoxy and/or $C_{1-8}$-alkylthio radicals,
$R^{11}$, $R^{12}$ independently of each other are H; $C_{1-18}$ alkyl, $C_{1-18}$ alkyl which is interrupted by one or more oxygen atoms; $C_{2-18}$ alkenyl, $C_{2-18}$ alkenyl which is interrupted by one or more oxygen atoms; $C_{3-12}$ cycloalkyl, phenyl-$C_{1-4}$-alkyl, phenyl, naphthyl or pyridyl, wherein these ring systems can be unsubstituted or substituted by 1 to 5 halogen atoms, $C_{1-8}$-alkyl, $C_{1-8}$-alkoxy and/or $C_{1-8}$-alkylthio radicals, or $R^{11}$ and $R^{12}$ together form a 5 or 6-membered O, S or N-containing heterocyclic ring which for its part can be anellated with an aliphatic or aromatic ring,
$R^1$, $R^2$ independently of each other are:

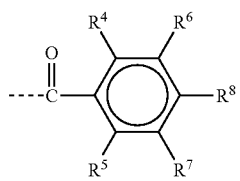

or H, or have one of the meanings given for $R^3$
wherein
$R^4$, $R^5$ independently of each other are H, halogen, a branched or linear $C_{1-6}$ alkyl or —O—$C_{1-6}$-alkyl radical which can be interrupted by one or more oxygen atoms;
$R^6$, $R^7$, $R^8$ independently of each other are H, halogen, a branched, cyclic or linear $C_{1-20}$ alkyl, -alkenyl, -alkyloxy or -alkenoxy radical, which can be interrupted by one or more O, S or —NR'— and can be substituted by one or more polymerizable groups and/or radicals $R^9$, wherein R' is H, halogen, a branched, cyclic or preferably linear $C_{1-20}$ alkyl, -alkenyl, -alkyloxy or -alkenoxy radical;
wherein $R^9$ is defined as above;

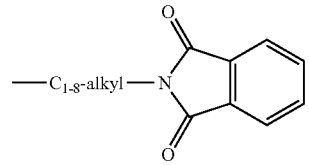

and
$R^3$ is a branched or linear $C_{1-18}$ alkyl radical or $C_{2-18}$ alkenyl radical, wherein these radicals can be unsubstituted or substituted one or more times by a radical which is selected from the following group: —OR$^{10}$, —SR$^{10}$, —OCO—R$^{10}$, —COO—R$^{10}$, —CH=CH—CO—OR$^{10}$, halogen, CN,

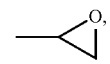

—C(C$_{1-4}$-alkyl)=C(C$_{1-4}$-alkyl)-CO—OR$^{10}$, —CO—R$^{13}$, —CO—CH=CH—CO—C$_{1-6}$-alkyl, —CO—CH=CH—CO-phenyl, —CO—CH=CH—COO—C$_{1-118}$-alkyl, —NR$^{11}$R$^{12}$, —N(R$^{11}$)—CO—R$^{10}$, —N(R$^{11}$)—COO—R$^{10}$, —N(R$^{11}$)—CO—NR$^{11}$R$^{12}$, —N(R$^{11}$)—CO-hal, —CO—NR$^{11}$R$^{12}$—SO$_2$—R$^{10}$, —SO$_2$—OR$^{10}$, —SO$_2$—NR$^{11}$R$^{12}$, —PO(OC$_{1-8}$-alkyl)$_2$, —SiR$^{14}$R$^{15}$R$^{16}$, —CH=CH-phenyl, —C(C$_{1-4}$-alkyl)=C(C$_{1-4}$ alkyl)phenyl, phenyl-C$_{1-4}$-alkyl, phenyl, naphthyl, biphenyl, C$_{5-12}$-cycloalkyl, a saturated or unsaturated 5 or 6-membered O, S or N-containing heterocyclic ring, benzophenonyl, thisanthonyl,
wherein
$R^{10}$, $R^{11}$ and $R^{12}$ are as defined above;
wherein
$R^{13}$ is $C_{1-18}$ alkyl, $C_{2-18}$ alkenyl which is interrupted by one or more O atoms, $C_{3-12}$ cycloalkyl, phenyl-$C_{1-4}$-alkyl, phenyl, naphthyl or biphenyl, wherein these ring systems can be unsubstituted or substituted by 1 to 5 $C_{1-8}$ alkyl, $C_{1-8}$ alkoxy, $C_{1-8}$ alkylthio radicals and/or halogen atoms;
$R^{14}$, $R^{15}$, $R^{16}$ independently of each other are H, $C_{1-8}$ alkyl, $C_{2-8}$ alkenyl, $C_{7-9}$ phenylalkyl, —O—$C_{1-8}$-alkyl, phenyl or —O—SiR$^{17}$R$^{18}$R$^{19}$,
wherein
$R^{17}$, $R^{18}$, $R^{19}$ independently of each other are H, $C_{1-8}$ alkyl, $C_{2-8}$ alkenyl, $C_{7-9}$ phenylalkyl, —O—$C_{1-8}$-alkyl or phenyl,
or
$R^3$ is a branched or linear $C_{2-18}$ alkyl radical or a $C_{2-18}$ alkylene radical which is interrupted one or more times by —O—, —NH—, —NR$^{11}$—, —S—, wherein the radicals can be unsubstituted or substituted one or more times by a radical which is chosen from the following group: halogen, CN, —OR$^{10}$, —SR$^{10}$, —OCO—R$^{10}$, —COO—R$^{10}$, —NR$^{11}$R$^{12}$—N(R$^{11}$)—CO—R$^{10}$, —N(R$^{11}$)—COO—R$^{10}$, —N(R$^{11}$)—CO—NR$^{11}$R$^{12}$, —N(R$^{11}$)—CO-hal, —CO—NR$^{11}$R$^{12}$, —SO$_2$—R$^{10}$, —SO$_2$—OR$^{10}$, —SO$_2$—NR$^{11}$R$^{12}$—PO(OC$_{1-8}$-alkyl)$_2$, —SiR$^{14}$R$^{15}$R$^{16}$, phenyl-C$_{1-4}$-alkyl, phenyl, C$_{5-12}$ cycloalkyl;

wherein R$^{10}$, R$^{11}$, R$^{12}$, R$^{14}$, R$^{15}$ and R$^{16}$ are as defined above;

or

R$^3$ is a branched or linear C$_{2-18}$ alkyl radical or a C$_{2-18}$ alkylene radical which is interrupted one or more times by —CO—, —COO—, —OCO—, —OCOO—, —CO—N(R$^{12}$)—, —N(R$^{12}$)—CO—, —N(R$^{12}$)—CO—N(R$^{12}$)—, —N(R$^{12}$)—COO—, —COO—C$_{1-6}$-alkylene, —COS—C$_{1-18}$-alkylene, —SO$_2$—, —SO$_2$—O—, —SO$_2$—N(R$^{12}$)—, —(CH$_3$)$_2$Si[OSi(CH$_3$)$_2$]$_q$—, with q=1 to 6; phenyl-C$_{1-4}$-alkylene, phenylene, naphthylene, biphenylene, C$_{5-12}$ cycloalkylene or a 5 or 6-membered O, S or N-containing heterocyclic ring;

wherein R$^{12}$ is defined above;

or

R$^3$ is trimethylsilyl, hal-(CH$_3$)$_2$Si—[OSi(CH$_3$)$_2$]$_r$—, (CH$_3$)$_3$Si—[OSi(CH$_3$)$_2$]$_r$ with r=1 to 6, —COOH, —COO—R$^{10}$, —CO—NR$^{11}$R$^{12}$, —CO-vinyl, —CO-phenyl, wherein the phenyl radical can be unsubstituted or substituted by —CH$_3$, —OCH$_3$ and/or —Cl;

wherein R$^{10}$, R$^{11}$ and R$^{12}$ are as defined above;

or

R$^3$ is phenyl-C$_{1-20}$-alkyl, phenyl, naphthyl or biphenyl, C$_{5-12}$ cycloalkyl or a saturated or unsaturated 5 or 6-membered O, S or N-containing heterocyclic ring, wherein these ring systems can be unsubstituted or substituted by 1 to 5 halogen atoms, C$_{1-8}$ alkyl, C$_{1-8}$ alkoxy, C$_{1-8}$ alkylthio radicals and/or —NR$^{11}$R$^{12}$, wherein R$^{11}$ and R$^{12}$ are as defined above, and m is 1, 2 or 3, n is 0 or 1, p is 0 or 1;

or

R$^3$ is halogen, OH, an aromatic C$_{6-30}$ radical which can be substituted by a branched, cyclic or linear C$_{1-20}$ alkyl, -alkenyl, -alkoxy or -alkenoxy radical, wherein the radicals can be interrupted by one or more O, S or N atoms and/or can be substituted by one or more polymerizable groups and/or radicals R$^9$, or is a branched, cyclic or linear C$_{1-20}$-alkyl, -alkenyl, -alkoxy or -alkenoxy radical which can be interrupted one or more times by O, S or —NR$^{20}$— and substituted by one or more polymerizable groups and/or radicals R$^9$, wherein R$^9$ is —OH, —C$_x$F$_{2x+1}$ with x=1 to 20, —[Si(CH$_3$)$_2$]$_y$—CH$_3$ with y=1 to 20, and R$^{20}$ is H, halogen, a branched, cyclic or linear C$_{1-20}$-alkyl, -alkenyl, -alkyloxy or -alkenoxy radical; and wherein two of the radicals R$^0$, R$^1$, R$^2$ or R$^3$ can be connected to each other to form a 5 to 8-membered ring, wherein the ring or rings can be anellated with one or more aliphatic or aromatic rings, unsubstituted or substituted one or more times and can contain further heteroatoms.

According to a further aspect, the present invention provides a composition with at least one polymerizable binder and at least one polymerization initiator, the composition comprising at least one acylgermanium compound according to Formula (II),

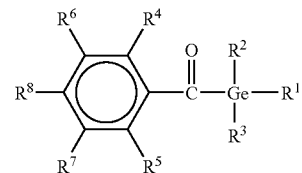

Formula (II)

in which

R$^1$, R$^2$ independently of each other are

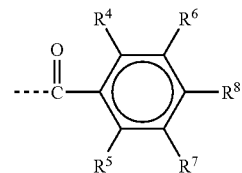

or H, or have one of the meanings given for R$^3$;

R$^3$ is halogen, OH, an aromatic C$_{6-30}$ radical which can be substituted by a branched, cyclic or linear C$_{1-20}$ alkyl, -alkenyl, -alkoxy or -alkenoxy radical, wherein the named radicals can be interrupted one or more times by O, S or —NR$^{20}$— and/or can be substituted by one or more polymerizable groups and/or radicals R$^9$, or is a branched, cyclic or preferably linear C$_{1-20}$ alkyl, -alkenyl, -alkoxy or -alkenoxy radical which can be interrupted one or more times by O, S or —NR$^{20}$— and can be substituted by one or more polymerizable groups and/or radicals R$^9$;

R$^4$, R$^5$ independently of each other are H, halogen, a linear or branched C$_{1-6}$ alkyl or —O—C$_{1-6}$ alkyl radical;

R$^6$, R$^7$, R$^8$ independently of each other are H, halogen, a branched, cyclic or linear C$_{1-20}$ alkyl, -alkenyl, -alkyloxy or -alkenoxy radical which is interrupted one or more times by O, S or —NR$^{20}$— and can be substituted by one or more polymerizable groups and/or radicals R$^9$;

R$^9$ is —OH, —C$_x$F$_{2x+1}$ with x=1 to 20, —[Si(CH$_3$)$_2$]$_y$—CH$_3$ with y=1 to 20; and R$^{20}$ is H, halogen, a branched, cyclic or linear C$_{1-20}$ alkyl, -alkenyl, -alkyloxy or -alkenoxy radical.

According to yet another aspect, the present invention provides a composition with at least one polymerizable binder and at least one polymerization initiator, the composition comprising at least an acylgermanium compound according to Formula (III):

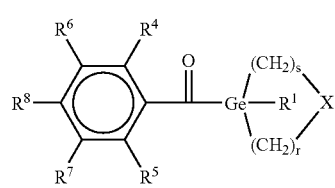

Formula (III)

in which
R¹ is

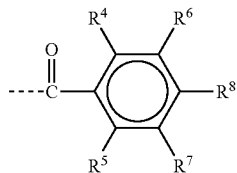

or H, or has one of the meanings given for R³;
r, s independently of each other are an integer from 0 to 6, wherein r and s are chosen such that the sum of the ring atoms including the germanium atom is 5 to 8, and
X is N—R²¹, O, S or is absent, wherein R²¹ is H or $C_{1-10}$ alkyl, and
wherein the germanium-containing ring can be anellated with one or more aliphatic or aromatic rings and can be unsubstituted or substituted one or more times whereby the number of hydrogen atoms of the ring is correspondingly reduced.

DETAILED DESCRIPTION

According to certain aspects of the invention, there are provided compositions with at least one polymerizable binder and at least one polymerization initiator, which contain at least one acylgermanium compound according to the general Formula (I),

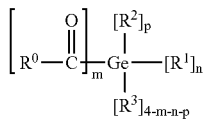

Formula (I)

in which
R⁰ is $C_{1-18}$ alkyl, $C_{2-18}$ alkenyl, wherein these radicals can be unsubstituted or substituted one or more times by halogen, —OR¹⁰, —OCO—R¹⁰, —OCO-hal, —COO—R¹⁰, —CH═CH—CO—OR¹⁰, —N(R¹¹)—CO—R¹⁰, —N(R¹¹)—CO-hal, —C($C_{1-4}$-alkyl)═C($C_{1-4}$-alkyl)-CO—OR¹⁰, —CO—NR¹¹R¹², —CH═CH phenyl, —C($C_{1-4}$-alkyl)═C($C_{1-4}$-alkyl)phenyl, $C_{3-12}$ cycloalkyl, $C_{2-18}$ alkenyl, phenyl-$C_{1-4}$-alkyl, phenyl, naphthyl, antryl, biphenyl, a saturated or unsaturated 5 or 6-membered O, S or N-containing heterocyclic ring, wherein all ring systems mentioned can be unsubstituted or substituted by 1 to 5 halogen atoms, $C_{1-8}$ alkyl, $C_{1-8}$ alkoxy and/or $C_{1-8}$ alkylthio radicals, or

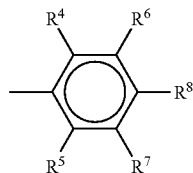

wherein
R¹⁰ is H; $C_{1-18}$ alkyl; $C_{1-18}$ alkyl which is interrupted by one or more oxygen atoms, $C_{2-18}$ alkenyl; $C_{2-18}$ alkenyl which is interrupted by one or more oxygen atoms; $C_{3-12}$ cycloalkyl; tetrahydropyran-2-yl, phenyl-$C_{1-20}$-alkylene; phenyl-$C_{1-20}$-alkenylene; $C_{1-6}$ alkyl which can be unsubstituted or substituted by halogen, cyclohexyl, cyclopentyl, tetrahydrofuranyl, furanyl or isopropyl-4-methyl-cyclohexyl; is phenyl; naphthyl or biphenyl; wherein these ring systems can be unsubstituted or substituted by 1 to 5 halogen atoms; $C_{1-8}$ alkyl; $C_{1-8}$ alkoxy and/or $C_{1-8}$ alkylthio radicals;

R¹¹, R¹² independently of each other are H; $C_{1-18}$ alkyl; $C_{1-18}$ alkyl which is interrupted by one or more oxygen atoms; $C_{2-18}$ alkenyl; $C_{2-18}$ alkenyl which is interrupted by one or more oxygen atoms; $C_{3-12}$ cycloalkyl; phenyl-$C_{1-4}$-alkyl; phenyl; naphthyl or pyridyl; wherein these ring systems can be unsubstituted or substituted by 1 to 5 halogen atoms, $C_{1-8}$ alkyl, $C_{1-8}$ alkoxy and/or $C_{1-8}$ alkylthio radicals; or R¹¹ and R¹² together form a 5 or 6-membered O, S or N-containing heterocyclic ring which for its part can be anullated with an aliphatic or aromatic ring, R¹, R² independently of each other are:

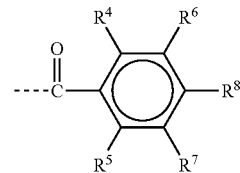

or H, or have one of the meanings given for R³; wherein R⁴, R⁵ independently of each other are in each case H, halogen, a branched or linear $C_{1-6}$ alkyl or —O—$C_{1-6}$-alkyl radical which can be interrupted by one or more oxygen atoms;

R⁶, R⁷, R⁸ independently of one another are in each case H, halogen, a branched, cyclic or preferably linear $C_{1-20}$ alkyl, -alkenyl, -alkyloxy or -alkenoxy radical, which can be interrupted by one or more O, S or —NR²⁰— and can be substituted by one or more polymerizable groups and/or radicals R⁹, wherein R²⁰ is H. halogen, a branched, cyclic or preferably linear $C_{1-20}$ alkyl, -alkenyl, -alkyloxy or -alkenoxy radical;

R³ is a branched or more preferably linear $C_{1-18}$ alkyl radical or $C_{2-18}$ alkenyl radical, wherein these radicals can be unsubstituted or substituted one or more times by a radical which is selected from the following group: halogen, CN,

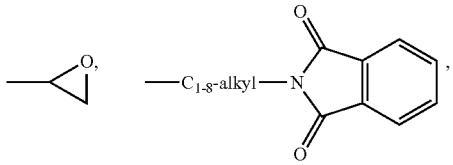

—OR¹⁰, —SR¹⁰, —OCO—R¹⁰, —COO—R¹⁰, —CH═CH—CO—OR¹⁰, —C($C_{1-4}$ alkyl)═C($C_{1-4}$-alkyl)-CO—OR¹⁰, —CO—R¹³, —CO—CH═CH—CO—$C_{1-6}$-alkyl, —CO—CH═CH—CO-phenyl, —CO—CH═CH—COO—$C_{1-18}$-alkyl, —NR¹¹R¹²—N(R¹¹)—CO—R¹⁰, —N(R¹¹)—COO—R¹⁰, —N(R¹¹)—CO—NR¹¹R¹², —N(R¹¹)—CO-hal, —CO—NR¹¹R¹², —SO₂—R¹⁰, —SO₂—OR¹⁰, —SO₂—NR¹¹R¹², —PO(O$C_{1-8}$-alkyl)₂, —SiR¹⁴R¹⁵R¹⁶, —CH═CH-phenyl, —C($C_{1-4}$-alkyl)=C($C_{1-4}$-alkyl)phenyl, phenyl-$C_{1-4}$-alkyl, phenyl, naphthyl, biphenyl, $C_{5-12}$-cycloalkyl, a saturated or unsaturated 5 or 6-membered O, S or N-containing heterocyclic ring, benzophenonyl, thisanthonyl, wherein $R^{13}$ is $C_{1-18}$ alkyl, $C_{2-18}$ alkenyl which is interrupted by one or more O atoms, $C_{3-12}$ cycloalkyl, phenyl-$C_{1-4}$ alkyl, phenyl, naphthyl or biphenyl, wherein the named ring systems can be unsubstituted or substituted by 1 to 5 $C_{1-8}$-alkyl, $C_{1-8}$ alkoxy, $C_{1-8}$ alkylthio radicals and/or halogen atoms;

$R^{14}$, $R^{15}$, $R^{16}$ independently of each other are in each case H, $C_{1-8}$ alkyl, $C_{2-8}$ alkenyl, $C_{7-9}$ phenylalkyl, —O—$C_{1-8}$-alkyl, phenyl or —O—Si$R^{17}R^{18}R^{19}$, wherein $R^{17}$, $R^{18}$, $R^{19}$ independently of each other are in each case H, $C_{1-8}$ alkyl, $C_{2-8}$ alkenyl, $C_{7-9}$ phenylalkyl, —O—$C_{1-8}$ alkyl or phenyl, and wherein $R^{10}$, $R^{11}$ and $R^{12}$ are as defined above;

or $R^3$ is a branched or more preferably linear $C_{2-18}$ alkyl radical or a $C_{2-18}$ alkylene radical which is interrupted one or more times by —O—, —NH—, —$NR^{11-}$, —S—, wherein the radicals can be unsubstituted or substituted one or more times by a radical which is chosen from the following group: halogen, CN, —$OR^{10}$, —$SR^{10}$, —OCO—$R^{10}$, —COO—$R^{10}$, —$NR^{11}R^{12}$, —$N(R^{11})$—CO—$R^{10}$, —$N(R^{11})$—COO—$R^{10}$, —$N(R^{11})$—CO—$NR^{11}R^{12}$, —$N(R^{11})$—CO-hal, —CO—$NR^{11}R^{12}$, —$SO_2R^{10}$, —$SO_2OR^{10}$, —$SO_2$ $NR^{11}R^{12}$, —PO(O$C_{1-8}$-alkyl)$_2$, —Si$R^{14}R^{15}R^{16}$, phenyl-$C_1$-alkyl, phenyl, $C_{5-12}$ cycloalkyl;

wherein $R^{10}$, $R^{11}$, $R^{12}$, $R^{14}$, $R^{15}$ and $R^{16}$ are as defined above;

or $R^3$ is a branched or more preferably linear $C_{2-18}$ alkyl radical or a $C_{2-18}$ alkylene radical, which is interrupted one or more times by —CO—, —COO—, —OCO—, —OCOO—, —CO—$N(R^{11})$—, —$N(R^{11})$—CO—, —$N(R^{11})$—CO—$N(R^{11})$—, —$N(R^{11})$—COO—, —COO—$C_{1-6}$-alkylene, —COS—$C_{1-18}$-alkylene, —$SO_2$—, —$SO_2$—O—, —$SO_2$—$N(R^{11})$—, —$(CH_3)_2$ Si[OSi(CH$_3$)$_2$]$_q$—, with q=1 to 6; phenyl-$C_{1-4}$-alkylene, phenylene, naphthylene, biphenylene, $C_{5-12}$ cycloalkylene or a 5 or 6-membered O, S or N-containing heterocyclic ring;

wherein $R^{11}$ is as defined above;

or $R^3$ is trimethylsilyl, hal-(CH$_3$)$_2$Si—[OSi(CH$_3$)$_2$]$_r$, (CH$_3$)$_3$Si—[OSi(CH$_3$)$_2$]$_r$ with r=1 to 6, —COOH, —COO—$R^{10}$, —CO—$NR^{11}R^{12}$, —CO-vinyl, —CO-phenyl, wherein the phenyl radical can be unsubstituted or substituted by —CH$_3$, —OCH$_3$ and/or —Cl;

wherein $R^{10}$, $R^{11}$ and $R^{12}$ are as defined above;

or $R^3$ is phenyl-$C_{1-20}$-alkyl, phenyl, naphthyl or biphenyl, $C_{5-12}$ cycloalkyl or a saturated or unsaturated 5 or 6-membered O, S or N-containing heterocyclic ring, wherein these ring systems can be unsubstituted or substituted by 1 to 5 halogen atoms, $C_{1-8}$ alkyl, $C_{1-8}$ alkoxy, $C_{1-8}$ alkylthio radicals and/or —$NR^{11}R^{12}$ wherein $R^{11}$ and $R^{12}$ are as defined above and m is 1, 2 or 3, n is 0 or 1, p is 0 or 1;

or, according to certain embodiments $R^3$ is halogen, OH, an aromatic $C_{6-30}$ radical which can be substituted by a branched, cyclic or linear $C_{1-20}$ alkyl, -alkenyl, -alkoxy or -alkenoxy radical, wherein these radicals can be interrupted by one or more O, S or N-atoms and/or can be substituted by one or more polymerizable groups and/or radicals $R^9$, or is a branched, cyclic or preferably linear $C_{1-20}$ alkyl, -alkenyl, -alkoxy or -alkenoxy radical which can be interrupted one or more times by O, S or —$NR^{20}$— and can be substituted by one or more polymerizable groups and/or radicals $R^9$, wherein $R^9$ is —OH, —$C_xF_{2x+1}$ with x=1 to 20, —[Si(CH$_3$)$_2$]$_y$—CH$_3$ with y=1 to 20, and $R^{20}$ is H, halogen, a branched, cyclic or linear $C_{1-20}$ alkyl, -alkenyl, -alkyloxy or -alkenoxy radical.

Additionally, two of the radicals $R^0$, $R^1$, $R^2$ or $R^3$ can be connected to each other to form a 5 to 8-membered ring which for its part can be anellated with one or more, such as 1 or 2 aliphatic or aromatic rings. These rings can contain further heteroatoms in addition to the germanium atom, such as O, S or N atoms. The number of additional heteroatoms can be 1 or 2. Different radicals, or in the case of m, n, p or 4-m-n-p>1 also identical radicals, can be connected to each other to form one or more rings. For example in the case where p=2 the two radicals $R^2$ can be connected to each other. By the connection of the radicals cyclic germanium compounds are formed, i.e., compounds in which the germanium atom is integrated into a ring. If two times two groups are linked to each other then these are spiro compounds with germanium as central atom (spiro atom). The formed rings can be unsubstituted or substituted one or more times, such as once or twice. Possible substituents are $C_{1-4}$ alkyl groups or =O.

The variables preferably have the following meanings:

$R^0$ is $C_{1-18}$ alkyl, $C_{2-18}$ alkenyl, wherein these radicals can be unsubstituted or substituted one or more times by halogen, —$OR^{10}$, —OCO—$R^{10}$, —OCO-hal, —COO—$R^{10}$, —CH=CH—CO—$OR^{10}$, —$N(R^{11})$—CO—$R^{10}$, —$N(R^{11})$—CO-hal, —C($C_{1-4}$-alkyl)=C($C_{1-4}$-alkyl)-CO—$OR^{10}$, —CO—$NR^{11}R^{12}$, —CH=CH phenyl, —C($C_{1-4}$-alkyl)=C($C_{1-4}$-alkyl)phenyl, $C_{3-12}$ cycloalkyl, $C_{2-18}$ alkenyl, phenyl-$C_{1-4}$-alkyl, phenyl, naphthyl, antryl, biphenyl, a 5 or 6-membered O, S or N-containing heterocyclic ring, wherein all these ring systems can be unsubstituted or substituted by 1 to 5 halogen atoms, $C_{1-8}$ alkyl, $C_{1-8}$ alkoxy and/or $C_{1-8}$ alkylthio radicals, or

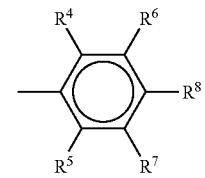

wherein $R^{10}$ is H, $C_{1-18}$ alkyl, $C_{2-18}$ alkenyl, $C_{2-18}$ alkenyl, which is interrupted by one or more oxygen atoms, $C_{3-12}$ cycloalkyl, tetrahydropyran-2-yl, phenyl-$C_{1-4}$-alkylene, phenyl-$C_{1-4}$-alkenylene, $C_{1-6}$ alkyl which can be unsubstituted or substituted by halogen, cyclohexyl, cyclopentyl, tetrahydrofuranyl, furanyl or isopropyl-4-methyl-cyclohexyl, is phenyl, naphthyl or biphenyl, wherein these ring systems can be unsubstituted or substituted by 1 to 5 halogen atoms, $C_{1-8}$ alkyl, $C_{1-8}$ alkoxy and/or $C_{1-8}$ alkylthio radicals, $R^{11}$, $R^{12}$ independently of each other are H, $C_{1-18}$ alkyl, $C_{2-18}$ alkenyl, $C_{2-18}$ alkenyl which is interrupted by one or more oxygen atoms, $C_{3-12}$ cycloalkyl, phenyl-$C_{1-4}$-alkyl, phenyl, naphthyl or pyridyl, wherein these ring systems can be unsubstituted or substituted by 1 to 5 halogen atoms, $C_{1-8}$ alkyl, $C_{1-8}$ alkoxy and/or $C_{1-8}$ alkylthio radicals, or $R^{11}$ and $R^{12}$ together form a 5 or 6-membered O, S or N-containing heterocyclic ring which for its part can be anellated with an aliphatic or aromatic ring, $R^1$, $R^2$ independently of each other are

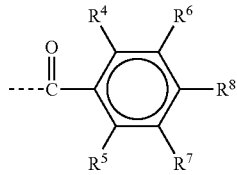

or H, or have one of the meanings given for $R^3$; wherein $R^4$, $R^5$ independently of each other are in each case H, halogen, a branched or linear $C_{1-6}$ alkyl or —O—$C_{1-6}$-alkyl radical;

$R^6$, $R^7$, $R^8$ independently of each other are in each case H, halogen, a branched, cyclic or preferably linear $C_{1-20}$ alkyl, -alkenyl, -alkyloxy or -alkenoxy radical, which can be interrupted by one or more O, S or —NR'— and can be substituted by one or more polymerizable groups and/or radicals $R^9$, wherein R' is H, halogen, a branched, cyclic or preferably linear $C_{1-20}$ alkyl, -alkenyl, -alkyloxy or -alkenoxy radical;

$R^3$ is a branched or linear $C_{1-8}$ alkyl radical or $C_{2-18}$ alkenyl radical, wherein these radicals can be unsubstituted or substituted one or more times by a radical which is selected from the following group:

halogen, CN,

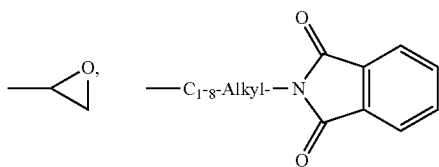

—$OR^{10}$, —$SR^{10}$, —OCO—$R^{10}$, —COO—$R^{10}$, —CH═CH—CO—$OR^{10}$, —C($C_{1-4}$ alkyl)═C($C_{1-4}$-alkyl)-CO—$OR^{10}$, —CO—$R^3$, —CO—CH═CH—CO—$C_{1-6}$-alkyl, —CO—CH═CH—CO-phenyl, —CO—CH═CH—COO—$C_{1-18}$-alkyl, —$NR^{11}R^{12}$, —N($R^{11}$)—CO—$R^{10}$, —N($R^{11}$)—COO—$R^{10}$, —N($R^{11}$)—CO—$NR^{11}R^{12}$, —N($R^{11}$)—CO-hal, —CO—$NR^{11}R^{12}$, —$SO_2$—$R^{10}$, —$SO_2$—$OR^{10}$, —$SO_2$—$NR^{11}R^{12}$, —PO(O$C_{1-8}$-alkyl)$_2$, —$SiR^{14}R^{15}R^{16}$, —CH═CH-phenyl, —C($C_{1-4}$-alkyl)═C($C_{1-4}$-alkyl)phenyl, phenyl-$C_{1-4}$-alkyl, phenyl, naphthyl, biphenyl, $C_{5-12}$ cycloalkyl, a 5 or 6-membered O, S or N-containing heterocyclic ring, benzophenonyl, thisanthonyl, wherein $R^{13}$ is $C_{1-18}$ alkyl, $C_{2-18}$ alkenyl which is interrupted by one or more O atoms, $C_{3-12}$ cycloalkyl, phenyl-$C_{1-4}$ alkyl, phenyl, naphthyl or biphenyl, wherein these ring systems can be unsubstituted or substituted by 1 to 5 $C_{1-8}$-alkyl, $C_{1-8}$ alkoxy, $C_{1-8}$ alkylthio radicals and/or halogen atoms;

$R^{14}$, $R^{15}$, $R^{16}$ independently of each other are in each case H, $C_{1-8}$ alkyl, $C_{2-8}$ alkenyl, $C_{7-9}$ phenylalkyl, —O—$C_{1-8}$-alkyl, phenyl or —O—$SiR^{17}R^{18}R^{19}$, wherein $R^{17}$, $R^{18}$, $R^{19}$ independently of each other are in each case H, $C_{1-8}$ alkyl, $C_{2-8}$ alkenyl, $C_{7-9}$ phenylalkyl, —O—$C_{1-8}$ alkyl or phenyl, and wherein $R^{10}$, $R^{11}$ and $R^{12}$ are as defined above;

or $R^3$ is a branched or preferably linear $C_{2-18}$ alkyl radical or a $C_{2-18}$ alkylene radical which is interrupted one or more times by —O—, —NH—, —$NR^{11}$—, —S—, wherein the radicals can be unsubstituted or substituted one or more times by a radical which is chosen from the following group:

halogen, CN, —$OR^{10}$, —$SR^{10}$, —OCO—$R^{10}$, —COO—$R^{10}$, —$NR^{11}R^{12}$, —N($R^{11}$)—CO—$R^{10}$, —N($R^{11}$)—COO—$R^{10}$, —N($R^{11}$)—CO—$NR^{11}R^{12}$, —N($R^{11}$)—CO-hal, —CO—$NR^{11}R^{12}$, —$SO_2$—$R^{10}$, —$SO_2$—$OR^{10}$, —$SO_2$—$NR^{11}R^{12}$, —PO(O$C_{1-8}$-alkyl)$_2$, —$SiR^{14}R^{15}R^{16}$ phenyl-$C_{1-4}$-alkyl, phenyl, $C_{5-12}$ cycloalkyl;

wherein $R^{10}$, $R^{11}$, $R^{12}$, $R^{14}$, $R^{15}$ and $R^{16}$ are as defined above;

or $R^3$ is a branched or linear $C_{2-18}$ alkyl radical or a $C_{2-18}$ alkylene radical, which is interrupted one or more times by —CO—, —COO—, —OCO—, —OCOO—, —CO—N($R^{12}$)—, —N($R^{12}$)—CO—, —N($R^{12}$)—CO—N($R^{12}$)—, —N($R^{12}$)—COO—, —COO—$C_{1-6}$-alkylene, —COS—$C_{1-18}$-alkylene, —$SO_2$—, —$SO_2$—O—, —$SO_2$—N($R^{12}$)—, —(CH$_3$)$_2$Si[OSi(CH$_3$)$_2$]$_q$—, with q=1 to 6; phenyl-$C_{1-4}$-alkylene, phenylene, naphthylene, biphenylene, $C_{5-12}$ cycloalkylene or a 5 or 6-membered O, S or N-containing heterocyclic ring;

wherein $R^{12}$ is as defined above;

or $R^3$ is trimethylsilyl, hal-(CH$_3$)$_2$Si—[OSi(CH$_3$)$_2$]$_r$—, (CH$_3$)$_3$Si—[OSi(CH$_3$)$_2$]$_r$— with r=1 to 6, —COOH, —COO—$R^{10}$, —CO—$NR^{11}R^{12}$, —CO-vinyl, —CO-phenyl, wherein the phenyl radical can be unsubstituted or substituted by —CH$_3$, —OCH$_3$ and/or —Cl;

wherein $R^{10}$, $R^{11}$ and $R^{12}$ are as defined above;

or $R^3$ is phenyl-$C_{1-4}$-alkyl, phenyl, naphthyl or biphenyl, $C_{5-12}$ cycloalkyl or a 5 or 6-membered O, S or N-containing heterocyclic ring, wherein these ring systems can be unsubstituted or substituted by 1 to 5 halogen atoms, $C_{1-8}$ alkyl, $C_{1-8}$ alkoxy, $C_{1-8}$ alkylthio radicals and/or —$NR^{11}R^{12}$, wherein $R^{11}$ and $R^{12}$ are as defined above and m is 1, 2 or 3, n is 0 or 1, p is 0 or 1;

or, according to certain embodiments $R^3$ is halogen, OH, an aromatic $C_{6-30}$ radical which can be substituted by a branched, cyclic or preferably linear $C_{1-20}$ alkyl, -alkenyl, -alkoxy or -alkenoxy radical, wherein the named radicals can be interrupted by one or more O, S or N atoms and/or can be substituted by one or more polymerizable groups and/or radicals $R^9$, or is a branched, cyclic or preferably linear $C_{1-20}$ alkyl, -alkenyl, -alkoxy or -alkenoxy radical which can be interrupted one or more times by O, S or —$NR^{20}$— and can be substituted by one or more polymerizable groups and/or radicals $R^9$, wherein $R^9$ is —OH, —$C_xF_{2x+1}$ with x=1 to 20, -[Si(CH$_3$)$_2$]$_y$—CH$_3$ with y=1 to 20, and $R^{20}$ is H, halogen, a branched, cyclic or preferably linear $C_{1-20}$ alkyl, -alkenyl, -alkyloxy or -alkenoxy radical.

Acylgermanium compounds of the Formula (I) are mono-, bis-, or triacylgermanium compounds, wherein mono- and bisacylgermanium compounds are preferred.

According to additional embodiments of the invention, compounds according to the following Formula (II) are provided:

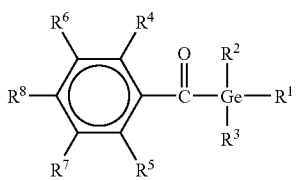

Formula (II)

in which
$R^1$, $R^2$ independently of each other are:

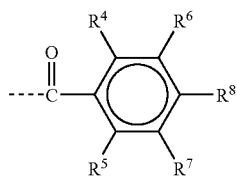

or H, or have one of the meanings given for $R^3$;

$R^3$ is halogen, OH, an aromatic $C_{6-30}$ radical which can be substituted by a branched, cyclic or preferably linear $C_{1-20}$ alkyl, -alkenyl, -alkoxy or -alkenoxy radical, wherein the named radicals can be interrupted by one or more O, S or N-atoms and/or substituted by one or more polymerizable groups and/or radicals $R^9$, or a branched, cyclic or preferably linear $C_{1-20}$ alkyl, -alkenyl, -alkoxy or -alkenoxy radical which can be interrupted one or more times by O, S or —NR$^{20}$— and can be substituted by one or more polymerizable groups and/or radicals $R^9$;

$R^4$, $R^5$ independently of each other are in each case H, halogen, a branched or linear $C_{1-6}$ alkyl or —O—$C_{1-6}$ alkyl radical;

$R^6$, $R^7$, $R^8$ independently of each another are in each case H, halogen, a branched, cyclic or preferably linear $C_{1-20}$ alkyl, -alkenyl, -alkyloxy or -alkenoxy radical which is interrupted one or more times by O, S or —NR$^{20}$— and can be substituted by one or more polymerizable groups and/or radicals $R^9$;

$R^9$ is —OH, —$C_xF_{2x+1}$ with x=1 to 20, —[Si(CH$_3$)$_2$]$_y$—CH$_3$ with y=1 to 20; and $R^{20}$ is H, halogen, a branched, cyclic or preferably linear $C_{1-20}$ alkyl, -alkenyl, -alkyloxy or -alkenoxy radical.

Germanium compounds according to further embodiments of the present invention defined by following Formula (III) may also be provided:

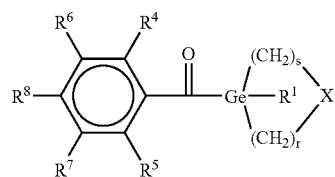

Formula (III)

in which
$R^1$ is

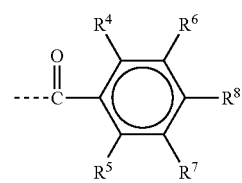

or H, or has one of the meanings given for $R^3$;

r, s independently of each other are an integer from 0 to 6, preferably 1 to 3, wherein r and s are chosen such that the sum of the ring atoms including the germanium atom is 5 to 8, and X is N—$R^{21}$, O, S or is absent, wherein $R^{21}$ is H or $C_{1-10}$ alkyl, preferably H or $C_{1-4}$ alkyl.

The germanium-containing ring can be anellated with one or more, such as 1 or 2 aliphatic or aromatic rings and be unsubstituted or substituted one or more times, such as once or twice, whereby the number of hydrogen atoms of the ring is correspondingly reduced. Substituents include $C_{1-4}$ alkyl groups or =O. Compounds of the Formula (III) in which the germanium-containing ring is not anellated with further rings and is unsubstituted apart from $R^{21}$ are also contemplated.

All stereoisomeric forms and mixtures of various stereoisomeric forms such as, e.g., racemates are covered by Formula (I) and the other formulae shown here. The formulae cover only those compounds that conform to the chemical valence theory.

The indication that a radical can be interrupted by a heteroatom such as 0 is to be understood to mean that the O atoms are inserted into the carbon chain of the radical, i.e. are bordered on both sides by carbon atoms. The number of O atoms is therefore smaller than the number of carbon atoms by at least 1 and the O atoms cannot be terminal. According to certain embodiments of the invention, radicals which are not interrupted by O atoms are contemplated.

Halogen (abbreviated to hal) includes F, Cl, Br or I, in particular F, Cl, quite particularly Cl.

Polymerizable groups which may be present as substituents in the above radicals are vinyl, styryl, (meth)acrylate, (meth)acrylamide and/or N-alkylacrylamide, particularly preferably (meth)acrylate, (meth)acrylamide and/or N-alkylacrylamide. The radicals $R^2$, $R^3$, $R^6$, $R^7$ and $R^8$ are preferably substituted with 0 to 3, in particular 0 to 1 polymerizable groups. The polymerizable groups are preferably arranged terminally.

According to the invention those compounds of the general Formulae (I) and (II) in which the variables can have the following meanings, that can be chosen independently of each another:

$R^1$ 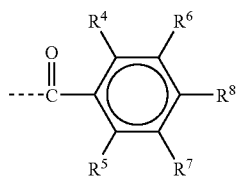 or H, or one of the meanings given for $R^2$ and $R^3$;

$R^2$, $R^3$ independently of each other a linear $C_{1-4}$ alkyl or alkenyl radical which can be substituted by one or more polymerizable groups;

$R^4$, $R^5$ independently of each other in each case H, halogen, a branched or linear $C_{1-4}$ alkyl or —O—$C_{1-4}$ alkyl radical;

$R^6$, $R^7$, $R^8$ independently of each other in each case H, halogen, a linear $C_{1-20}$ alkyl, -alkenyl, -alkoxy or -alkenoxy radical which can be interrupted by one or more —O—, —S— or —$NR^{20}$— radicals and are substituted by one or more polymerizable groups.

Alternative definitions of the variables which likewise can be chosen independently of one another are:

$R^1$ 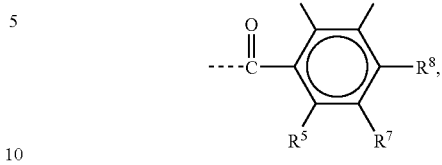 or one of the meanings given for $R^2$ and $R^3$;

$R^2$, $R^3$ $C_1$-$C_4$ alkyl;

$R^4$, $R^5$, $R^8$ H, Cl, $CH_3$, $OCH_3$;

$R^6$, $R^7$ H, $C_1$-$C_4$ alkyl which can be interrupted by one or more O atoms.

Specific compounds of Formula (II) in which $R^2=R^3$, $R^4=R^5$ and/or $R^6=R^7$ are also contemplated Those acylgermanium compounds according to Formula (I) and in particular Formula (II) which contain 0 to 2, or 0, or 1, polymerizable group can be provided. The individual radicals of Formula (I) may contain 0 to 4, or 0 to 2, polymerizable groups.

Specific examples of exemplary compounds are:

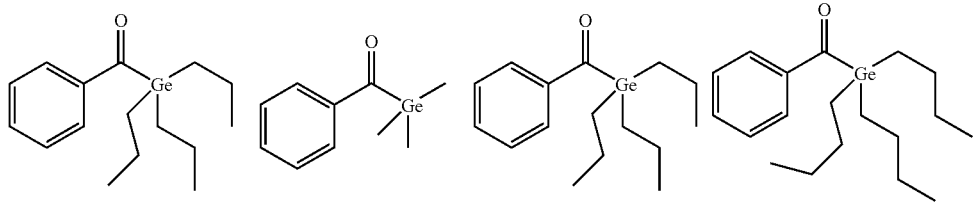

benzoyltriethylgermanium   benzoyltrimethylgermanium   benzoyltripropylgermanium   benzoyltributylgermanium

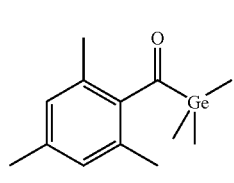 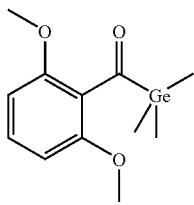 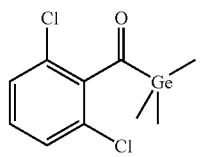

(2,4,6-trimethylbenzoyl)trimethylgermanium   (2,6-dimethoxybenzoyl)trimethylgermanium   (2,6-dichlorobenzoyl)trimethylgermanium

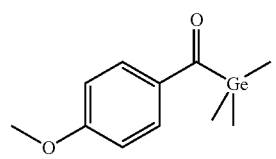 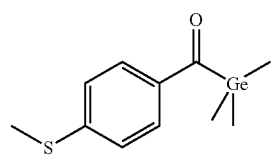 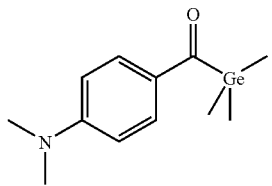

(4-methoxybenzoyl)trimethylgermanium   (4-methylsulpfanylbenzoyl)trimethylgermanium   (4-dimethylaminobenzoyl)trimethylgermanium

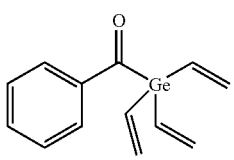 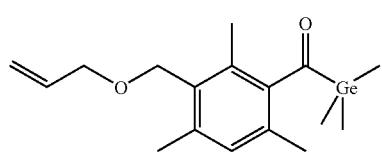

benzoyltrivinylgermanium   (3-allyloxymethyl-2,4,6-trimethylbenzoyl)trimethylgermanium -continued

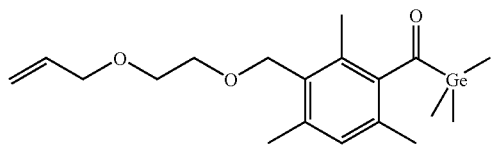

[3-(2-allyloxy-ethoxymethyl)-2,4,6-trimethylbenzoyl]trimethylgermanium

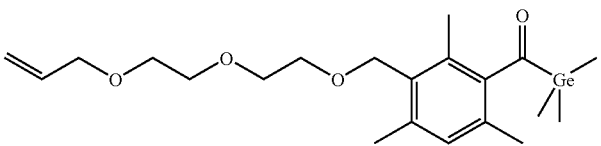

{3-[2-(2-allyloxy-ethoxy)-ethoxy]-ethoxymethyl]-2,4,6-trimethylbenzoyl}trimethylgermanium

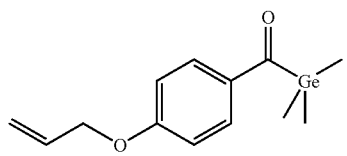

(4-allyloxy-benzoyl)trimethylgermanium

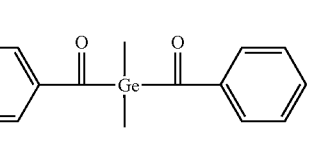

bisbenzoyldimethylgermanium

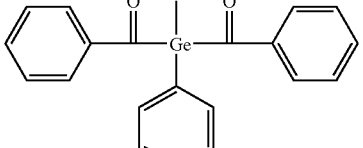

dibenzoylmethylphenylgermanium

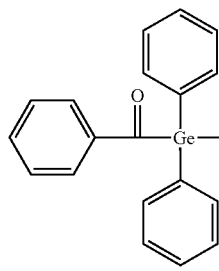

dibenzoyldiphenylgermanium

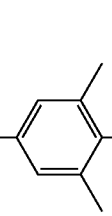

bis(2,4,6-trimethylbenzoyl)dimethylgermanium

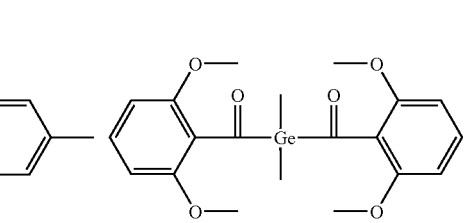

bis(2,6-dimethoxybenzoyl)dimethylgermanium

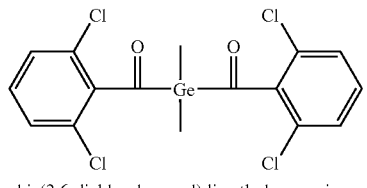

bis(2,6-dichlorobenzoyl)dimethylgermanium

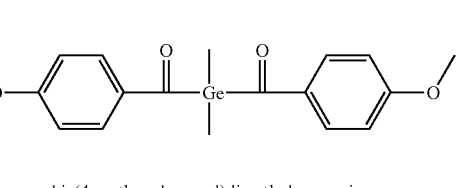

bis(4-methoxybenzoyl)dimethylgermanium

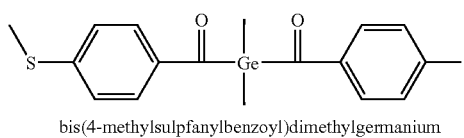

bis(4-methylsulfanylbenzoyl)dimethylgermanium

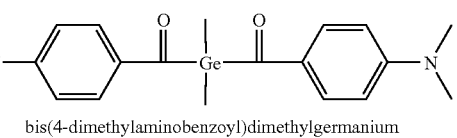

bis(4-dimethylaminobenzoyl)dimethylgermanium

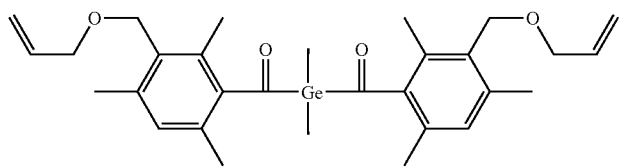

bis(3-allyloxymethyl-2,4,6-trimethylbenzoyl)dimethylgermanium

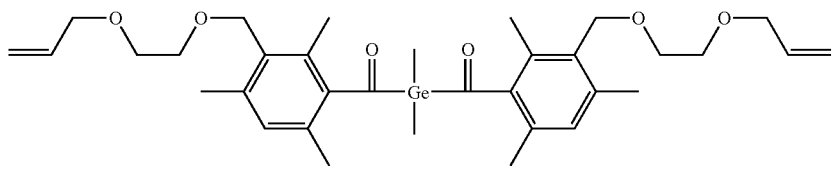

bis[3-(2-allyloxy-ethoxymethyl)-2,4,6-trimethylbenzoyl]dimethylgermanium

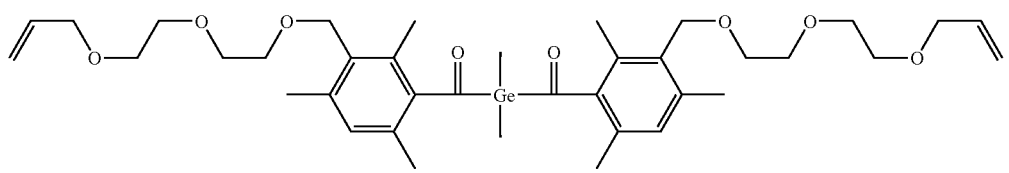

bis{3-[2-(2-allyloxy-ethoxy)-ethoxy]-ethoxymethyl]-2,4,6-trimethylbenzoyl}dimethylgermanium

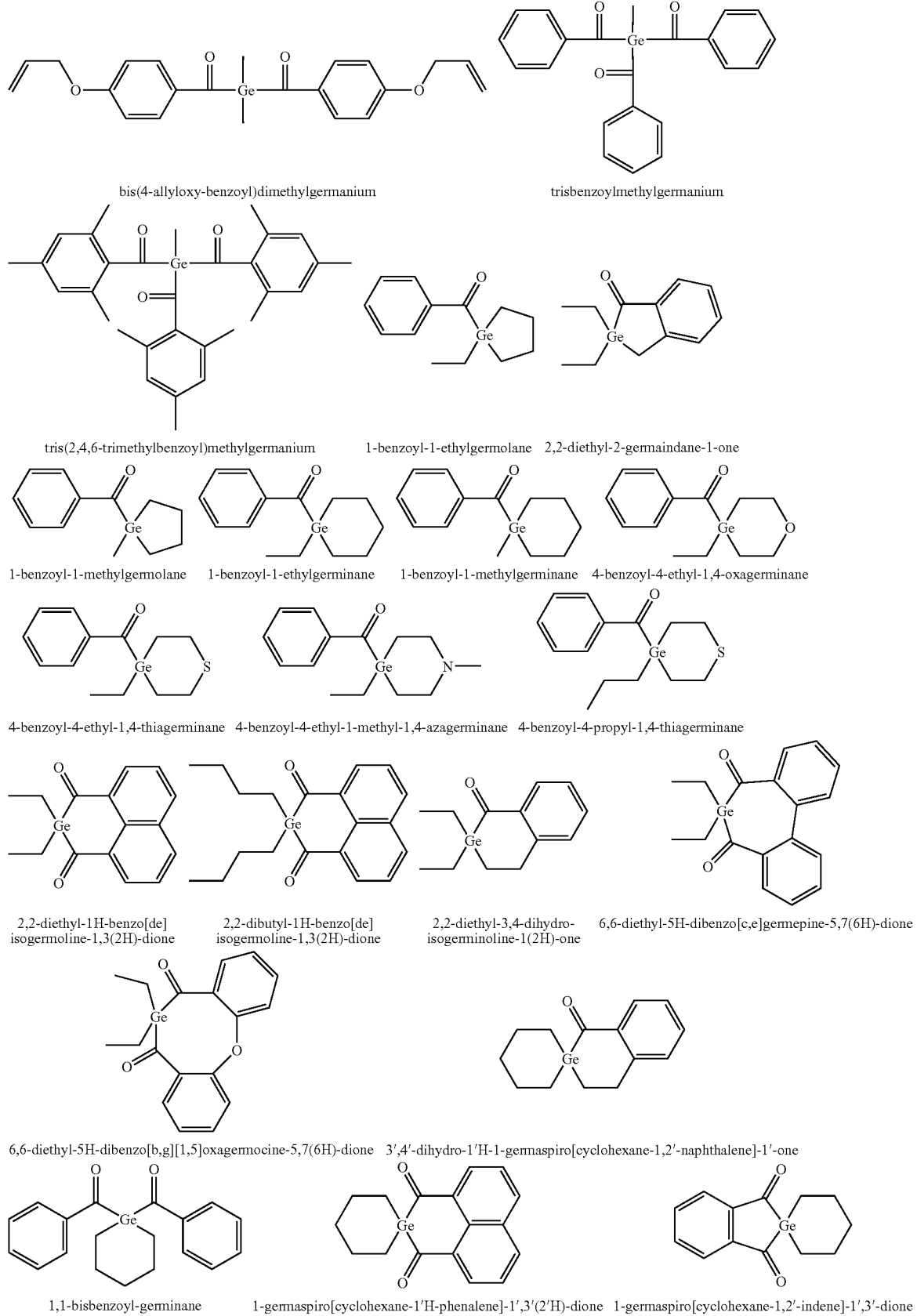

Additional exemplary compounds include:
(2,4,6-trimethylbenzoyl)triethylgermanium,
(2,4,6-trimethylbenzoyl)tripropylgermanium,
(2,4,6-trimethylbenzoyl)tributylgermanium, (2,6-dimethoxybenzoyl)triethylgermanium,
(2,6-dimethoxybenzoyl)tripropylgermanium,
(2,6-dimethoxybenzoyl)tributylgermanium, (2,6-dichlorobenzoyl)triethylgermanium,
(2,6-dichlorobenzoyl)tripropylgermanium, (2,6-dichlorobenzoyl)tributylgermanium,
bisbenzoyldiethylgermanium,
bisbenzoyldipropylgermanium,
bisbenzoyldibutylgermanium, bis(2,4,6-trimethylbenzoyl)diethylgermanium,
bis(2,4,6-trimethylbenzoyl)dipropylgermanium,
bis(2,4,6-trimethylbenzoyl)dibutylgermanium,
bis(2,6-dimethoxybenzoyl)diethylgermanium,
bis(2,6-dimethoxybenzoyl)dipropylgermanium,
bis(2,6-dimethoxybenzoyl)dibutylgermanium,
bis(2,6-dichlorobenzoyl)dibutylgermanium,
bis(2,6-dichlorobenzoyl)diethylgermanium,
bis(2,6-dichlorobenzoyl)dipropylgermanium,
bis(2,6-dichlorobenzoyl)dibutylgermanium, trisbenzoylethylgermanium, and
tris(2,4,6-trimethylbenzoyl)ethylgermanium, which are structurally similar to the compounds shown above.

The acylgermanium compounds used according to the invention of general Formula (I) are partly known already from the state of the art. Monoacylgermanes can be synthesized, e.g., according to a method by Yamamoto et. al. (Yamamoto, K.; Hayashi, A.; Suzuki, S.; Tsuji J.; Organometallics; 6 (1987) 974) by reacting hexaalkyldigermanium with acid chloride:

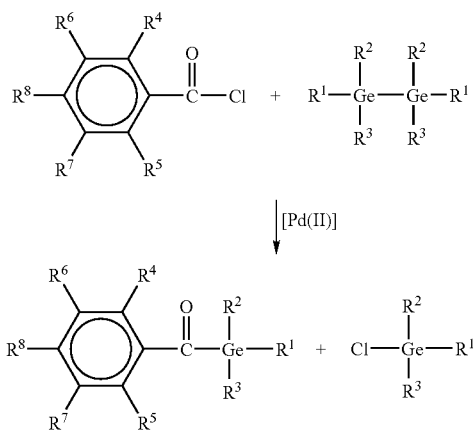

Specific example:

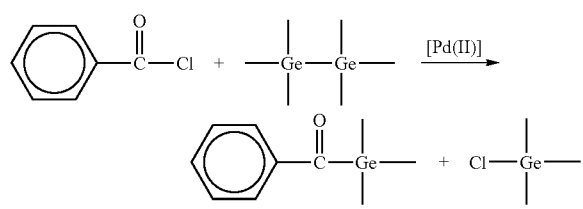

A further possibility for preparing bisacylgermanes is the reaction of the corresponding lithiated germanium compounds with acid chlorides according to Castel et. al. (Castel, A.; Riviere, P.; Satge, J.; Ko, H. Y.; Organometallics; 9 (1990) 205):

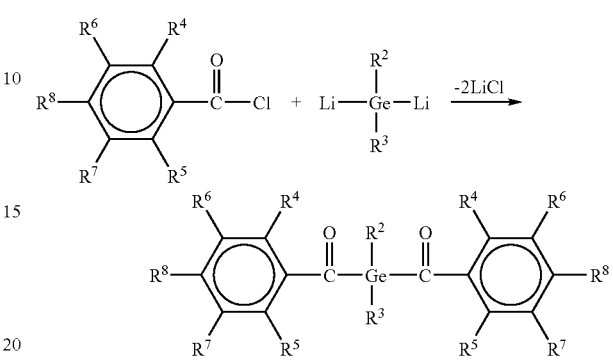

Specific example:

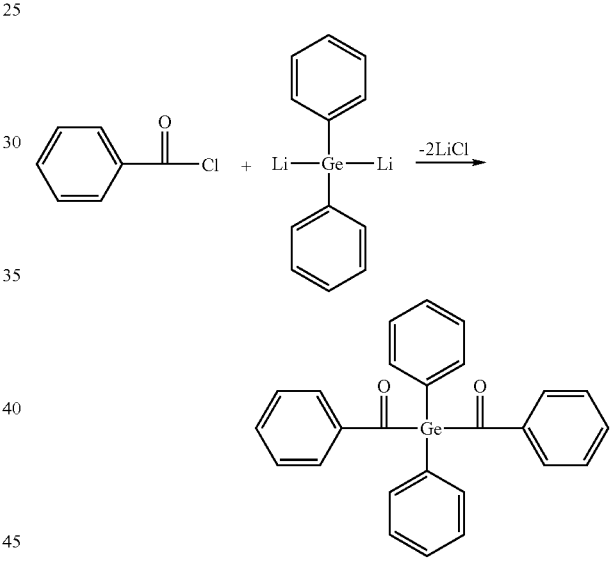

Lithiated aromatic germanium compounds can be prepared, e.g., by reacting the corresponding germanium halide (X=halogen) with lithium (Li) (Nishimura, T.; Inoue-Ando, S.; Sato, Y., J. Chem. Soc., Perkin Trans. 1; (1994) 1589) or hydrogermanium with n-butyllithium (BuLi) (Castel, A.; Riviere, P.; Satge, J.; Ko, H. Y.; Organometallics; 9 (1990) 205):

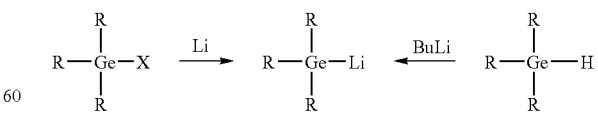

Furthermore mono- and bisacylgermanes can be synthesized by reacting a carbanion which is obtained from 1,3-dithians with germanium chlorides according to Brook et. al. (Brook, A. G.; Duff, J. M.; Jones, P. F.; Davis, N. R.; "Synthesis of Silyl and Germyl Ketones" J. Am. Chem. Soc. 89(2), 431-434 (1967)). This synthesis path is particularly suitable for the preparation of bisalkylbisacylgermanes:

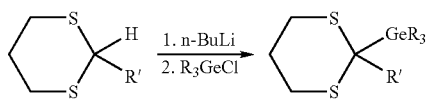

The dithians obtained can be hydrolyzed to form the corresponding ketones according to methods which are generally known to a person skilled in the art (according to Brook, A. G.; Duff, J. M.; Jones, P. F.; Davis, N. R.; "Synthesis of Silyl and Germyl Ketones" J. Am. Chem. Soc. 89(2), 431-434 (1967) or, e.g., also according to Sharma, H. K.; Cervanes-Lee, F.; Pannel, K. H.; "Organometalloidal derivatives of the transition metals, XXVII. Chemical and structural investigations on (ferrocenylacyl)germanes)," J. Organomet. Chem. 409, 321-330 (1991).

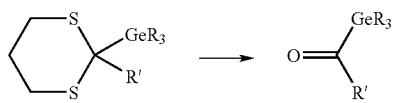

The acylgermanium compounds of general Formula (I) are particularly suitable as photoinitiators for polymerization, in particular as initiators for radical polymerization, photoaddition and for thiolene reaction (polyaddition). It was found with these initiators that, upon irradiation with light, preferably in the visible range, in particular with a wavelength of 400 to 500 nm, a high thorough-curing depth can be achieved compared with customary photoinitiators without the initiators resulting in colored materials. This is a great advantage in many technical and particularly medical materials, such as, e.g., dental materials and bone cements.

In addition, the acylgermanium compounds of Formula (I) used according to the invention are characterized by a lower cytotoxicity compared with customary initiators, which is likewise a particular advantage for medical applications. The acylgermanium compounds are therefore also particularly suitable, for example, as initiators for materials for the preparation of contact lenses but also for conventional optical lenses in which a low inclination of the initiators to discoloration is also of benefit.

The use of initiators of Formula (I) is not limited to medical applications. The great thorough-curing depth upon curing with light in the visible wavelength range is also a substantial advantage in technical applications. The compositions according to the invention are particularly suitable for a plurality of uses, such as for example as printing inks or paints, varnishes, adhesives, for the preparation of printing plates, integrated circuits, photoresists, soldering masks, inks for color printing, as materials for holographic data storage, for the preparation of nano-sized microelectromechanical elements, optical waveguides, pre-shaped parts and for the optical preparation of information carriers.

To initiate polymerization, the acylgermanium compounds of Formula (I) are irradiated, with light in the wavelength range of 200 to 750 nm, 200 to 550 nm, 300 to 550 nm, or 350 to 500 nm. They can thus be used as initiators for laser curing and laser-induced 3D curing and also for 2-photon polymerization. They are particularly suitable as initiators for pigmented systems as they make possible the use of absorption gaps of the pigment.

It is particularly advantageous that the initiators can also be activated with LED light sources. The wavelength of LEDs depends on the lattice constant of the substrate. The quality (thermal strength, heat expansion, constancy of the interatomic distances, etc.) of the substrate determines the level of the possible power of the LEDs. In intraoral use wavelengths are only permitted from approximately 380 nm so that initiators of Formula (I) which can be activated with a wavelength in the range of 380 nm or more are particularly suited for intraoral actuation.

Combinations of LED light sources with initiators according to Formula (I), or with compositions which contain such an initiator, are also a subject of the invention. Systems of LED light sources with a wavelength of 400 to 550 nm, 400 to 480 nm, or 450±20 nm, and initiators or compositions matched to this, i.e., initiators with an activation wavelength in the range from 400 to 550 nm, 400 to 480 nm, or approximately 450±20 nm, and compositions containing these, are suited for dental use. In addition, LED light sources with a wavelength of approximately 650±30 nm or approximately 360±30 nm, together with initiators or compositions matched to this, are provided according to the invention.

The compositions according to the invention preferably also contain, in addition to at least one acylgermanium compound of Formula (I), a polymerizable binder. Binders based on radically and/or cationically polymerizable monomers and/or prepolymers are contemplated.

Mono- or multifunctional (meth)acrylates or a mixture thereof are suitable as radically polymerizable binders. Monofunctional (meth)acrylic compounds comprise compounds with one polymerizable group. Multifunctional (meth)acrylic compounds comprise compounds with two or more, such as 2-3 polymerizable groups.

Examples of the above include methyl, ethyl, hydroxyethyl, butyl, benzyl, tetrahydrofurfuryl or isobornyl(meth) acrylate, bisphenol-A-di(meth)acrylate, bis-GMA (an addition product of methacrylic acid and bisphenol-A-diglycidylether), UDMA (an addition product of 2-hydroxyethyl methacrylate and 2,2,4-trimethylhexamethylene diisocyanate), di-, tri- or tetraethyleneglycol di(meth)acrylate, trimethylolpropane tri(meth)acrylate, pentaerythritol tetra(meth)acrylate as well as glycerol dimethacrylate, 1,4-butanediol di(meth)acrylate, 1,10-decanediol di(meth) acrylate or 1,12-dodecanediol di(meth)acrylate. Compositions which contain at least one radically polymerizable monomer with 2 or more, such as 2 to 3 radically polymerizable groups, are contemplated. Multifunctional monomers have cross-linking properties.

Hydrolysis-stable monomers such as hydrolysis-stable mono(meth)acrylates, e.g. mesityl methacrylate or 2-(alkoxymethyl)acrylic acids, e.g. 2-(ethoxymethyl)acrylic acid, 2-(hydroxymethyl)acrylic acid, N-mono- or -disubstituted acrylamides, such as N-ethyl acrylamide, N,N-dimethacrylamide, N-(2-hydroxyethyl)acrylamide, N-methyl-N-(2-hydroxyethyl)acrylamide or N-monosubstituted methacrylamides, such as N-ethyl methacrylamide or N-(2-hydroxyethyl)methacrylamide and moreover N-vinylpyrrolidone or allyl ether can also be used as radically polymerizable binders. Examples of hydrolysis-stable cross-linking monomers include urethanes of 2-(hydroxymethyl)acrylic acid and diisocyanates such as 2,2,4-trimethylhexamethylene diisocyanate or isophorone diisocyanate, cross-linking pyrrolidones such as, e.g., 1,6-bis(3-vinyl-2-pyrrolidonyl)-hexane, or commercially available bisacrylamides such as methylene or ethylene bisacrylamide, bis(meth)acrylamides such as N,N'-diethyl-1,3-bis(acrylamido)-propane, 1,3-bis(methacrylamido)-propane, 1,4-bis(acrylamido)-butane or 1,4-bis(acryloyl)-piperazine which can be synthesized by reaction from the corresponding diamines with (meth)acrylic acid chloride. Monomers that are liquid at room temperature, which can be used as diluting monomers, are contemplated.

Low-shrinkage radically ring-opening polymerizable monomers such as mono- or multifunctional vinyl cyclopropanes or bicylic cyclopropane derivatives, such as those described in DE 196 16 183 C2 or EP 1 413 569, or cyclic allyl sulfides, or those described in U.S. Pat. No. 6,043,361 and U.S. Pat. No. 6,344,556, can furthermore also be used as radically polymerizable binders. These can also be used in combination with the previously mentioned di(meth)acrylate cross-linkers. Exemplary ring-opening polymerizable monomers include vinyl cyclopropanes such as 1,1-di(ethoxycarbonyl)- or 1,1-di(methoxycarbonyl)-2-vinyl cyclopropane, the esters of 1-ethoxycarbonyl- or 1-methoxycarbonyl-2-vinyl cyclopropane carboxylic acid with ethyleneglycol, 1,1,1-trimethylolpropane, 1,4-cyclohexanediol or resorcin. Exemplary bicyclic cyclopropane derivatives include 2-(bicyclo [3.1.0]hex-1-yl)acrylic acid methyl or ethyl esters, their disubstitution products in 3 position (3,3-bis(ethoxycarbonyl)bicyclo[3.1.0]hex-1-yl)acrylic acid methyl or ethyl ester. Preferred cyclic allyl sulfides are the addition products of 2-(hydroxymethyl)-6-methylene-1,4-dithiepan or 7-hydroxy-3-methylene-1,5-dithiacylooctane with 2,2,4-trimethylhexamethylene-1,6-diisocyanate or the asymmetric hexamethylene diisocyanate trimers (Desmodur® VP LS 2294 from Bayer AG).

Moreover, styrene, styrene derivatives or divinyl benzole, unsaturated polyester, polyurethane and epoxy resins and allyl compounds or radically polymerizable polysiloxanes which can be prepared from suitable methacrylic silanes such as 3-(methacryloyloxy)propyltrimethoxysilane and are described, e.g., in DE 199 03 177 C2 can be used as radically polymerizable binders.

Furthermore, mixtures of the previously named monomers with radically polymerizable, acid-group-containing monomers which are also called adhesive monomers can be used as radically polymerizable binders. Preferred acid-group-containing monomers are polymerizable carboxylic acids such as maleic acid, acrylic acid, methacrylic acid, 2-(hydroxymethyl)acrylic acid, 4-(meth)acryloyloxyethyltrimellic acid anhydride, 10-methacryloyloxydecylmalonic acid, N-(2-hydroxy-3-methacryloyloxypropyl)-N-phenylglycine or 4-vinylbenzoic acid.

Radically polymerizable phosphonic acid monomers, in particular vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl-acrylic acid or 2-[2-dihydroxyphosphoryl)-ethoxymethyl]-acrylic acid ethyl or 2,4,6-trimethylphenyl ester are also suitable as adhesive monomers.

Furthermore, acidic polymerizable phosphoric acid esters, in particular 2-methacryloyloxypropyl mono- or dihydrogen phosphate, 2-methacryloyloxyethyl mono- or dihydrogen phosphate, 2-methacryloyloxyethylphenyl hydrogen phosphate, dipentaerythritol-pentamethacryloyloxyphosphate, 10-methacryloyloxydecyl-dihydrogen phosphate, dipentaerythritol-pentamethacryloyloxyphosphate, phosphoric acid mono-(1-acryloyl-piperidine-4-yl)-ester, 6-(methacrylamido)hexyl dihydrogen phosphate and 1,3-bis-(N-acryloyl-N-propyl-amino)-propane-2-yl-dihydrogen phosphate are suitable as adhesive monomers.

In addition, polymerizable sulphonic acids are suitable as adhesive monomers, in particular vinyl sulphonic acid, 4-vinylphenyl sulphonic acid or 3-(methacrylamido)propyl sulphonic acid.

Thiol-ene resins which contain mixtures of mono- or multifunctional mercapto compounds and di- or multifunctional unsaturated monomers, above all allyl or norbornene compounds are suitable as binders curable by polyaddition.

Examples of mono- or multifunctional mercapto compounds include o, m or p-dimercaptobenzene and esters of thioglycol or of 3-mercaptopropionic acid of ethylene, propylene or butylene glycol, hexanediol, glycerol, trimethylolpropane or pentaerythritol.

Examples of di- or multifunctional allyl compounds include esters of allyl alcohol with di- or tricarboxylic acids such as malonic, maleic, glutaric, succinic, adipic, sebacic, phthalic, terephthalic or gallic acid and mono- or trifunctional allyl ethers such as, diallyl ether, $\alpha,\omega$-bis[allyloxy]alkane, resorcin or hydroquinone diallyl ether and pyrogallol triallyl ether, or other compounds such as 1,3,5-triallyl-1,3,5-triazine-2,4,6-(1H,3H,5H)-trione, tetraallylsilane or tetraallylorthosilicate.

Examples of di- or multifunctional norbornene compounds are Diels-Alder addition products of cyclopentadiene or furan with di- or multifunctional (meth)acrylates, and esters and urethanes of 5-norbornene-2-methanol or 5-norbornene-2-ol with di- or polycarboxylic acids such as, e.g., malonic, maleic, glutaric, succinic, adipic, sebacic, phthalic, terephthalic or gallic acid, with di- or polyisocyanates, such as hexamethylene diisocyanate or its cyclic trimer, 2,2,4-trimethylhexamethylene diisocyanate, toluoylene diisocyanate or isophorone diisocyanate.

Furthermore acylgermanium compounds of Formula (I) can be used as coinitiators or photosensitizers for the cationic polymerization of cationically polymerizable monomers. Exemplary cationically polymerizable diluting or cross-linking monomers are, e.g., glycidylether or cycloaliphatic epoxides, cyclic ketene acetals, vinyl ethers, spiroorthocarbonates, oxetanes or bicyclic ortho esters. Particular examples include: triethyleneglycol divinyl ether, cyclohexanedimethanol divinyl ether, 2-methylene-1,4,6-trioxaspiro[2.2]nonane, 3,9-dimethylene-1,5,7,11-tetraoxaspiro[5.5] undecane, 2-methylene-1,3-dioxepane, 2-phenyl-4-methylene-1,3-dioxolane, bisphenol-A-diglycidylether, 3,4-epoxy-cyclohexylmethyl-3,4-epoxycyclohexanecarboxylate, bis(-(3,4-epoxycyclohexylmethyl)adipate, vinylcyclohexene dioxide, 3-ethyl-3-hydroxymethyloxetane, 1,10,-decanediylbis (oxymethylene)bis(3-ethyloxetane) or 3,3-(4-xylylenedioxy)-bis-(methyl-3-ethyloxetane).

Silicic acid polycondensates, which are accessible for example by hydrolytic condensation of silanes which carry cationically polymerizable groups, such as epoxide, oxetane, spiroortho esters and/or vinyl ether groups, are also particularly suitable as cationically polymerizable binders. Such silicic acid polycondensates are for example described in DE 41 33 494 C2 or U.S. Pat. No. 6,096,903.

In addition to acylgermanium compounds of the general Formula (I), the compositions according to the invention can additionally also contain known photoinitiators (cf. J. P. Fouassier, J. F. Rabek (Ed.), Radiation Curing in Polymer Science and Technology, Vol. II, Elsevier Applied Science, London and New York 1993) for the UV or visible range, such as e.g.: benzoin ether, dialkyl benzil ketals, dialkoxyacetophenones, acyl or bisacyl phosphine oxides, $\alpha$-diketones such as 9,10-phenanthrenequinone, diacetyl, furil, anisil, 4,4'-dichlorobenzil and 4,4'-dialkoxybenzil and camphorquinone and if necessary coinitiators such as tertiary amines, e.g., dimethylaminobenzoic acid ethyl ester or methyldiethanolamine.

Moreover, in addition to the acylgermanium compounds of the general Formula (I) the compositions according to the invention can additionally contain one or more cationic photoinitiators, preferably diaryliodonium or triarylsulphonium salts. Preferred diaryliodonium salts are the commercially available photoinitiators 4-octyloxy-phenyl-phenyl-iodonium hexafluoroantimonate, isopropylphenyl-methylphenyl-iodoniumtetrakis(pentafluorophenyl)borate and 4-phenylsulphanylphenyl diphenylsulphonium hexafluorophosphate. These cationic photoinitiators can be used to accelerate the curing of compositions according to the invention based on acylgermanium compounds of the general Formula (I). Conversely, the curing of compositions with cationic initiators can be accelerated by adding acylgermanium compounds of the Formula (I).

Furthermore, the compositions according to the invention may also contain azo compounds such as 2,2'-azobis(isobutyronitrile) (AIBN) or azobis-(4-cyanovaleric acid), or peroxides such as dibenzoyl peroxide, dilauroyl peroxide, tert-butylperoctoate, tert-butylperbenzoate or di-(tert-butyl)-peroxide in addition to the acylgermanium compounds of general Formula (I) for dual curing. To accelerate initiation by means of peroxides, combinations with aromatic amines can be used. Preferred redox systems are combinations of benzoyl peroxide with amines such as N,N-dimethyl-p-toluidine, N,N-dihydroxyethyl-p-toluidine, p-dimethylaminobenzoic acid ethyl ester or structurally related systems. In addition, redox systems consisting of peroxides and reductants such as ascorbic acid, barbiturates or sulphinic acids are also suitable for dual curing. The quantity of additional initiators is about 0 to 3 wt. %.

According to the invention compositions are preferred which contain one or more fillers, preferably organic or inorganic particulate fillers. Preferred inorganic particulate fillers are amorphous spherical nanoparticulate fillers based on oxides such as pyrogenic silica or precipitated silica, $ZrO_2$ and $TiO_2$ or mixed oxides of $SiO_2$, $ZrO_2$ and/or $TiO_2$ with an average particle diameter of 10 to 200 nm, mini fillers such as quartz, glass ceramic or glass powder with an average particle size of 0.2 to 5 µm and x-ray opaque fillers such as ytterbium trifluoride, nanoparticulate tantalum(V) oxide or barium sulphate. In addition, fibrous fillers such as nanofibres, glass fibers, polyamide or carbon fibres can also be used.

The compositions according to the invention can contain coloring agents such as dyestuffs and/or pigments as further components.

Additionally, the compositions according to the invention can if necessary contain further additives and solvents, such as water, ethanol, acetone and/or ethyl acetate.

Optional additives may include stabilizers, UV absorbers, slip additives, wetting agents, dispersants, adhesion promoters, matting and brightening agents, leveling agents and film-forming auxiliaries, antiskinning agents, light-protection agents, corrosion-protection agents, flame retardants, anti-oxidants, optical brighteners, flow improvers, thickeners and anti-foaming agents.

The initiators according to Formulae (I) and (II) are characterized by a high reactivity and can therefore be used in low concentrations (cf. Example 7). Additionally they permit the curing also of thin layers or films without the formation of an inhibition layer. The initiators according to the invention can therefore be used to prevent the formation of an inhibition layer.

The compositions according to the invention preferably contain, relative to the total mass of the composition, 0.001 to 5 wt. %, 0.01 to 4 wt. %, 0.1 to 3 wt. % acylgermanium compound of Formula (I). Materials according to the invention thus may contain:
 (a) 0.001 to 5 wt.-%, 0.01 to 4 wt. %, or 0.1 to 3 wt. % acylgermanium compound of general Formula (I),
 (b) 5 to 99.9 wt. %, 10 to 95 wt. %, or 15 to 90 wt. % polymerizable binder, and
 (c) 0 to 90 wt.-%, 5 to 87 wt. %, or 10 to 85 wt. % filler.

The compositions can additionally advantageously contain:
 (d) 0 to 50 wt. %, 0.01 to 4 wt. %, or 0.1 to 3 wt. % additive, wherein these quantity details are relative to the total mass of all the additives, and
 (e) 0 to 10 wt.-%, or 0.01 to 5 wt. % pigments and/or dyestuffs.

All percentages relate to the total mass of the composition if not stated otherwise.

Compositions according to the invention are suitable as adhesives, coatings, varnishes, inks, cements, composites, for the preparation of pre-shaped parts or moldings such as rods, plates, disks, optical lenses, contact lenses and in particular as dental materials, quite particularly as filling composites.

Compositions for use as dental cements may contain:
 (a) 0.001 to 3 wt. % acylgermanium compound of general Formula (I),
 (b) 20 to 70 wt. % polymerizable binder,
 (c) 30 to 75 wt. % filler and
 (d) 0.01 to 5 wt. % additive.

Compositions for use as dental composites may contain:
 (a) 0.001 to 2 wt. % acylgermanium compound of general Formula (I),
 (b) 10 to 60 wt. % polymerizable binder,
 (c) 40 to 85 wt. % filler and
 (d) 0.01 to 5 wt. % additive.

Compositions for use as dental coating materials may contain:
 (a) 0.001 to 5 wt. % acylgermanium compound of general Formula (I),
 (b) 20 to 99.9 wt. % polymerizable binder,
 (c) 0 to 20 wt. % nanoparticulate fillers and
 (d) 0.01 to 2 wt. % additive,
 (e) 0 to 50 wt. % solvent.

Compositions for use as printing inks may contain:
 (a) 0.001 to 5 wt. % acylgermanium compound of general Formula (I),
 (b) 30 to 60 wt. % polymerizable binder,
 (c) 1 to 45 wt. % coloring agent and
 (d) 0.01 to 30 wt. % additive.

Compositions for use as varnish, for example as white varnish or as varnish for optical fibres, may contain:
 (a) 0.001 to 5 wt. % acylgermanium compound of general Formula (I),
 (b) 55 to 99.5 wt. % polymerizable binder,
 (c) 0.1 to 50 wt. % pigment, and optionally
 (d) 0.01 to 30 wt. % additive.

A suitable pigment for the preparation of varnishes is $TiO_2$.

Dental materials which can be cured by thiolene reaction preferably contain a mixture of one or more polythiol compounds and one or more polyvinyl compounds, wherein one or more of these compounds can be present in oligomeric form. Optionally, 45 to 55% of the functional groups of these mixtures are thiol groups, the remaining groups can be vinyl groups. The mixtures can furthermore contain one or more fillers, wherein the quantity of polymerizable resins can be 10 to 40 wt. %, and the filler quantity can be 60 to 90 wt. %.

Suitable mixtures of polythiol and polyvinyl compounds and suitable filler-containing mixtures are described in WO 2005/086911. The quantity of initiator according to Formula (I) can be 0.05 to 0.5 wt. %.

An additional aspect of the invention is the use of acylgermanes of Formula (I) for the preparation of adhesives, coatings, varnishes, inks, cements, composites, pre-shaped parts or dental materials and their use as initiators for radical polymerization.

The invention also relates to a process for the preparation of moldings, in particular dental crowns, bridges, inlays and artificial teeth, in which a composition according to the invention is molded into the molding in a manner known per se and then at least partially, or completely, cured. Curing preferably takes place through radical polymerization.

The photoinitiators according to the invention are characterized in particular by a high reactivity and a high activity already at low use concentration. An extremely rapid curing of the photopolymer can thereby be achieved compared with known photoinitiators which absorb in the visible range. For example, measurements of bisacyl diethylgermanium in a resin mixture of decanediol dimethacrylate ($D_3MA$):UDMA:bis-GMA=1:1:1 resulted in almost double the polymerization rate ($R_p$) of camphorquinone in combination with an amine accelerator in the same formulation. The curing time could likewise be halved compared with campherquinone/amine. Even with a 15-fold dilution of bisacyl diethylgermanium, a reactivity comparable with camphorquinone/amine as photoinitiator can still be achieved (see examples, Tables 7, 8, 9, sum of initiator and accelerator).

Moreover, the naturally yellow-colored photoinitiators according to Formula (I) have an outstanding photobleaching effect, i.e., the compounds of Formula (I) are decolorized upon curing and discolorations of the material after curing are thereby avoided (see examples, Table 2).

The invention is described in further detail below with reference to the following illustrative, non-limiting examples.

EXAMPLES

Example 1

Synthesis of Benzoyltrimethylgermanium 1.64 g (4.49 mmol) allyl palladium(II)chloride dimer, 1.49 g (8.97 mmol) triethylphosphite and 23.24 g (98.7 mmol) hexamethyldigermanium were placed in a dry 50-ml three-necked flask with reflux cooler and septum under argon and stirred for 5 min at room temperature. 12.62 g (89.7 mmol) freshly-distilled benzoyl chloride was then added dropwise. After stirring for 4 h at 110° C., the Pd catalyst was separated off from the reaction mixture and volatile reaction products and the excess hexamethyldigermanium drawn off at a rotary evaporator. The reaction mixture was separated off by column chromatography (petroleum ether (PE): ethyl acetate (EE)= 40:1). 7.8 g (78% of the theoretical value) benzoyltrimethylgermanium was obtained as yellow liquid. DC (petroleum ether: ethyl acetate=20:1): $R_f$=0.58.

UV-VIS: $\lambda_{max}$: 411.5 nm, $\epsilon$=1374 $dm^2$/mol $^1$H-NMR (200 MHz; $CDCl_3$): $\delta$ (ppm): 7.78-7.82 (m, 2H, Ar—$H^{2,6}$), 7.48-7.58 (m, 3H, Ar—$H^{3,4,5}$), 0.51 (s, 9H, —$CH_3$). $^{13}$C-NMR (200 MHz; $CDCl_3$): $\delta$ (ppm): 234.39 (—C=O), 140.61 (Ar—$C^1$), 132.90 (Ar—$C^4$), 128.75 (Ar—$C^{2,6}$), 127.71 (Ar—$C^{3,5}$), −1.14 (—$CH_3$). IR ($cm^{-1}$): 2979, 2916, 1628 (C=O), 1582, 1448, 1310, 1239, 1207, 1172, 905, 827, 770, 732.

Example 2

Synthesis of diethylbis-(2-phenyl-1,3-dithian-2-yl)germanium 1.85 g (9.42 mmol) 2 phenyl-1,3-dithian was placed in a dry 50-ml three-necked flask under argon and dissolved in 28 ml anhydrous THF. 3.99 ml 2.36 M BuLi solution in hexane was added dropwise at 0° C. and the reaction solution stirred for 2 h at 0° C. 0.83 mg (3.93 mmol) diethyldichlorogermanium dissolved in 8 ml anhydrous THF was added slowly dropwise at 0° C. to the reaction mixture and then stirred for an additional 2 h at 0° C. To complete the reaction a further solution of 2-phenyl-2-lithium-1,3-dithian (2.36 mmol) was prepared as described above and added dropwise at 0° C. to the reaction solution, which was then stirred for 18 h at 6° C. The reaction was quenched by the addition of 20 ml water and the raw product extracted with diethyl ether (3×30 ml). The combined organic phases were dried with $Na_2SO_4$ and the solvent drawn off at the rotary evaporator. The residue was separated off by column chromatography (petroleum ether: ethyl acetate=20:1). 1.42 g (70% of the theoretical value) diethylbis(2-phenyl-1,3-dithian-2-yl)germanium was obtained as colorless solid. DC (petroleum ether: ethyl acetate=20:1): $R_f$=0.51

Melting point: 112-115° C. $^1$H-NMR (200 MHz; $CDCl_3$): $\delta$ (ppm): 7.82-7.86 (m, 4H, Ar—$H^{2,6}$), 7.01-7.24 (m, 6H, Ar—$H^{3,4,5}$), 2.55-2.69 (m, 4H, S—$CH_2$—), 2.12-2.23 (m, 4H, S—$CH_2$—), 1.63-2.01 (m, 4H—$CH_2$—), 1.19 (m, 4H, Ge—CH2-), 1.02 (m, 6H—$CH_3$). $^{13}$C-NMR (200 MHz; $CDCl_3$): $\delta$ (ppm): 140.58 (Ar—$C^1$), 130.38 (Ar—$C^4$), 128.18 (Ar—$C^{2,6}$), 125.53 (Ar—$C^{3,5}$), 51.90 (Ge—C—S), 25.88 (S—$CH_2$—), 25.16 (—$CH_2$—), 10.26 (Ge—$CH_2$—), 4.74 (—$CH_3$).

Example 3

Synthesis of Bisbenzoyidiethylgermanium 1.12 g (2.24 mmol) diethylbis-(2-phenyl-1,3-dithian-2-yl) germanium was placed in a 25-ml round-bottomed flask and dissolved in 15 ml aqueous THF (THF:water 4:1). After adding 3.53 g (35.01 mmol) $CaCO_3$ the suspension was stirred for 5 min at room temperature. 6.83 g (26.93 mmol) iodine was added in portions accompanied by light protection. After 3 h stirring at room temperature the reaction mixture was diluted with 15 ml diethyl ether and excess iodine decomposed by the addition of 20 ml of a saturated $Na_2S_2O_4$ solution accompanied by strong stirring. The resulting salts were separated off from the reaction solution by filtration with Hyflo and washed with diethyl ether (3×15 ml). The combined organic phases were dried with $Na_2SO_4$, filtered off, and the solvent drawn off at the rotary evaporator. The residue was separated off by column chromatography (petroleum ether: ethyl acetate 20:1). 0.46 g (60% of the theoretical value) of bisbenzoyldiethylgermanium was obtained as yellow solid. DC (petroleum ether:ethyl acetate=20:1): $R_f$=0.42

UV-VIS: $\lambda_{max}$: 418.5 nm, $\epsilon$=4880 $dm^2$/mol $^1$H-NMR (200 MHz; $CDCl_3$): $\delta$ (ppm): 7.70-7.75 (m, 2H, Ar—$H^{2,6}$), 7.37-7.50 (m, 3H, Ar—$H^{3,4,5}$), 1.50 (d, 4H, —$CH_2$), 1.11 (t, 6H, —$CH_3$). $^{13}$C-NMR (200 MHz; $CDCl_3$): $\delta$ (ppm): 230.22 (—C=O), 141.23 (Ar—$C^1$), 133.66 (Ar—$C^4$), 129.06 (Ar—$C^{2,6}$), 128.720 (Ar—$C^{3,5}$), 9.11 (—$CH_2$), 6.61 (—$CH_3$). IR ($cm^{-1}$): 2959, 2911, 1622 (C=O), 1579, 1447, 1308, 1207; 1169, 1022, 892, 767, 688

Compared with long-wave absorbing Norrish type I photoinitiators (=photoinitiators whose monomolecular photolysis generates directly polymerization-initiating radicals), such as the commercial bisacylphosphine oxide Irgacure 819 (bis(2,4,6-trimethylbenzoyl)-phenyl phosphine oxide) with the longest-wave absorption maxima at 397 nm, the maximum of the Norrish type I photoinitiator benzoyltrimethylgermanium at 411.5 nm or the maximum of bisbenzoyldiethylgermanium at 418.5 nm is clearly more bathochromic, which significantly improves the thorough curing depth of the photopolyreaction products. Only the group of the splitting titanocenes have a maximum at approximately 480 nm, however these are known to have an inadequate photobleaching effect, which results in orange-colored polymers (K. Dietliker; Photoinitiators for Free Radical, Cationic and Anionic Photopolymerization 2nd Ed. Sita Technology Ld, London UK pp. 228-239).

Compared with the Norrish type II photoinitiator camphorquinone ($\lambda_{max}$: 468 nm) widely used in dentistry, which requires an additional reductant for efficient radical formation, the absorption maximum of benzoyltrimethylgermanium is clearly shorter-wave and displays very good photobleaching upon irradiation.

Example 4

Preparation of a Composite Cement Using the Benzoyltrimethylgermanium from Example 1

Corresponding to Table 1 given below, composite fixing cements were prepared based on a methacrylate mixture and incorporating either various concentrations of the benzoyltrimethylgermanium from Example 1 (cement A to C) or a mixture of camphorquinone and p-N,N-dimethylaminobenzoic acid ethyl ester (cement D, comparison) by means of a roll mill ("Exakt" model, Exakt Apparatebau, Norderstedt). The cements B and D contained the same molar concentration of photoinitiator, i.e., of benzoyltrimethylgermanium (cement B) or camphorquinone (cement D). Test pieces were prepared from the materials which were irradiated twice for 3 minutes with a dental light source (Spectramat®, Ivoclar Vivadent AG) and thereby cured. The bending strength, the bending E modulus and the exothermic time were determined according to ISO standard ISO 4049 (Dentistry—Polymer-based filling, restorative and luting materials). Additionally the yellow coloration of the uncured pastes and also of the cured cements was characterized according to the DIN standard 5033 "Farbmessung" [color measurement] using the Minolta CR-300 L*a*b* color measurement system with the help of the b* value, wherein furthermore a b* value of −2.7 was measured for cement paste formulation without initiator components. Such measurements are contained in Table 2.

TABLE 1

Composition of the composite cements (details in wt.-%)

| Component | Cement A | Cement B | Cement C | Cement D[2] |
|---|---|---|---|---|
| Benzoyltrimethylgermanium | 0.10 | 0.32 | 0.50 | — |
| Camphorquinone | — | — | — | 0.24 |
| p-N,N-dimethylaminobenzoic acid ethyl ester | — | — | — | 0.23 |
| UDMA[1] | 32.11 | 31.89 | 31.71 | 31.80 |
| Triethyleneglycol dimethacrylate | 7.81 | 7.81 | 7.81 | 7.81 |
| Aerosil OX-50 (Degussa) | 41.27 | 41.27 | 41.28 | 41.23 |
| Ytterbium trifluoride (Rhone-Poulenc) | 18.71 | 18.71 | 18.70 | 18.69 |

[1]Addition product of 2 mol 2-hydroxyethylmethacrylate and 1 mol 2,2,4-trimethylhexamethylene diisocyanate
[2]Comparison

TABLE 2

Properties of composite cements

| Component | Cement A | Cement B | Cement C | Cement D[2] |
|---|---|---|---|---|
| Exothermic time (s) | 13 | 12 | 11 | 8 |
| Bending strength (MPa) after 24 h WI[1] | 102 | 116 | 129 | 118 |
| Elastic modulus (MPa) after 24 h WI[1] | 3230 | 5240 | 5560 | 5580 |
| b* value paste before curing | 7.7 | 16.0 | 19.6 | 27.4 |
| b* value cement after curing | −5.8 | −1.9 | 0.7 | 4.5 |

[1]WI = water immersion of the test piece at 37° C.
[2]Comparison

It is clear from Table 2 that the benzoyltrimethylgermanium-based cements with an increasing photoinitiator concentration result in a shorter exothermic time and thus a quicker curing and, compared with cement D (conventional photoinitiator mixture based on a mixture of camphorquinone and p-N,N-dimethylaminobenzoic acid ethyl ester), materials with comparable mechanical properties are obtained with a concentration of 0.32 wt. % benzoyltrimethylgermanium (cement B) and above. Surprisingly, it was found that the cured benzoyltrimethylgermanium-based cements display negative or only small positive b* values and thus no yellow coloration, while a b* value of 4.5 resulted for the cured camphorquinone-based cement, which corresponds to a clear yellow discoloration.

Example 5

Preparation of a Filler Composite Using the Benzoyltrimethylgermanium from Ex. 1

Corresponding to Table 3 given below, a filler composite was prepared based on a methacrylate mixture and incorporating either various concentrations of the benzoyltrimethylgermanium from Example 1 (composite E) or a mixture of camphorquinone and p-N,N-dimethylaminobenzoic acid ethyl ester (composite F, comparison) by means of a kneader (type LPM 0.1 SP, Linden, Marienheide). Analogous to Example 4, test pieces were prepared from the materials and cured. The bending strength, the bending E modulus and the polymerization shrinkage were determined according to ISO standard ISO 4049. Such measurements are contained in Table 4.

TABLE 3

Composition of the filler composites (details in wt.-%)

| Component | Composite E | Composite F[5] |
|---|---|---|
| Monomer resin[1] | 18.06 | 17.99 |
| Benzoyltrimethylgermanium | 0.08 | — |
| Camphorquinone | — | 0.05 |
| p-N,N-dimethylaminobenzoic acid ethyl ester | — | 0.09 |
| Glass filler GM27884 (Schott)[2] | 51.6 | 51.61 |
| Spherosil (Tokuyama Soda)[3] | 14.37 | 14.36 |

TABLE 3-continued

Composition of the filler composites
(details in wt.-%)

| Component | Composite E | Composite F[5] |
|---|---|---|
| Ytterbium trifluoride (Rhone-Poulenc) | 14.89 | 14.89 |
| OX-50[4] | 0.2 | 0.2 |

[1] Mixture of 42.4 wt.-% bis-GMA, 37.4 wt.-% UDMA and 20.2 wt.-% triethyleneglycol dimethacrylate
[2] Silanized Ba—Al-boron silicate glass filler with an average particle size of 1.5 µm,
[3] $SiO_2$—$ZrO_2$ mixed oxide, average primary particle size: 250 nm
[4] Silanized pyrogenic $SiO_2$ OX-50 (Degussa)
[5] Comparison

TABLE 4

Properties of filler composites

| Material property | Composite E | Composite F[2] |
|---|---|---|
| Exothermic time (s) | 10 | 9 |
| Bending strength (MPa) after 24 h WI[1] | 150 | 168 |
| Bending E modulus (GPa) after 24 h WI[1] | 10540 | 12190 |

[1] WI = water immersion of the test pieces at 37° C.
[2] Comparison

Example 6

Preparation of a Strongly Acidic Composite Cement Using the Benzoyltrimethylgermanium from Example 1

Corresponding to Table 5 given below, composite fixing cements were prepared based on a mixture of two dimethacrylates with the acidic phosphonic acid MA-154 (2-[2-dihydroxyphosphoryl)-ethoxymethyl]-acrylic acid ethyl ester and incorporating either the benzoyltrimethylgermanium from Example 1 (cement G) or a mixture of camphorquinone and p-N,N-dimethylaminobenzoic acid ethyl ester (cement H, comparison) by means of a roll mill ("Exakt" model, Exakt Apparatebau, Norderstedt). Analogous to Example 2, test pieces were prepared from the materials, cured, and the bending strength of the elastic modulus determined.

TABLE 5

Composition of the acidic composite cements
(details in wt.-%)

| Component | Cement G | Cement H[2] |
|---|---|---|
| Benzoyltrimethylgermanium | 0.33 | — |
| Camphorquinone | — | 0.24 |
| p-N,N-dimethylaminobenzoic acid ethyl ester | — | 0.23 |
| UDMA[1] | 21.88 | 21.82 |
| Triethyleneglycol dimethacrylate | 7.81 | 7.81 |
| Phosphonic acid MA-154 | 10.01 | 9.99 |
| Aerosil OX-50 (Degussa) | 41.27 | 41.22 |
| Ytterbium trifluoride (Rhone-Poulenc) | 18.70 | 18.69 |

[1] Addition product of 2 mol 2-hydroxyethylmethacrylate and 1 mol 2,2,4-trimethylhexamethylene diisocyanate
[2] Comparison

TABLE 6

Properties of the composite cements

| Component | Cement G | Cement H[2] |
|---|---|---|
| Bending strength (MPa) after 24 h WI[1] | 118 | 120 |
| Elastic modulus (MPa) after 24 h WI[1] | 5380 | 5690 |

[1] WI = water immersion of the test pieces at 37° C.
[2] Comparison

It is clear from Table 6 that the benzoyltrimethylgermanium-based cement G, compared with cement H (conventional photoinitiator mixture of a mixture of camphorquinone and p-N,N-dimethylaminobenzoic acid ethyl ester), also leads to materials with comparable mechanical properties in the presence of strongly acid monomers.

Example 7

Comparison of the Activity of Acylgermanes with Known Photoinitiators which Absorb in the Visible Range The activity of the photoinitiators was measured by means of photo-DSC (Differential Scanning Calorimetry) measurements on a DSC-50 device from Shimadzu, wherein the samples were irradiated alternatively with different dental lamps (Astalis 3: halogen lamp, wavelength range 400-500 nm, intensity 530 mW/cm$^2$; Bluephase C8: LED, wavelength range 430-490 nm, intensity 1100 mW/cm$^2$; Ivoclar Vivadent AG). The activity is characterized by the time of peak maximum ($t_{max}$), the polymerization rate ($R_P$) which corresponds to the peak height, and the double bond conversion (DBC). The respective photoinitiators were dissolved in a resin mixture of $D_3MA$:UDMA:bis-GMA=1:1:1 and then measured in an aluminum crucible by means of DSC.

Tables 7 and 8 show photo-DSC data of CQ (camphorquinone/dimethylaminobenzoic acid ethyl ester), Irg 819 (bis(2,4,6-trimethylbenzoyl)phenylphosphine oxide), benzoyltrimethylgermanium (Mono-AG) and bisbenzoyidiethylgermanium (Bis-AG) at a concentration of 0.022 mmol PI (photoinitiator) per gram of resin.

Table 9 shows photo-DSC data of Irg 819 (bis(2,4,6-trimethylbenzoyl)phenylphosphine oxide), benzoyltrimethylgermanium (Mono-AG) and bisbenzoyldiethylgermanium (Bis-AG) at different PI concentrations.

TABLE 7

| | Irradiation with an Astralis 3 lamp (400-500 nm) | | |
|---|---|---|---|
| PI | $t_{max}$ [s] | $R_p \times 10^{-3}$ [mol/(l × s)] | DBC [%] |
| CQ | 14 | 54.9 | 59 |
| Irg 819 | 11 | 67.5 | 59 |
| Mono-AG | 16 | 51.0 | 56 |
| Bis-AG | 7.8 | 99.2 | 84 |

TABLE 8

Irradiation with Bluephase C8 lamp (430-490 nm)

| PI | $t_{max}$ [s] | $R_p \times 10^{-3}$ [mol/(l × s)] | DBC [%] |
|---|---|---|---|
| CQ | 13 | 59.9 | 61 |
| Irg 819 | 17 | 43.5 | 45 |
| Mono-AG | 16 | 48.3 | 49 |
| Bis-AG | 7.8 | 98.5 | 72 |

TABLE 9

Activity comparison of different initiators

| Concentration [mmol/g] | PI | $t_{max}$ [s] | $R_p \times 10^{-3}$ [mol/(l × s)] | DBC [%] |
|---|---|---|---|---|
| 0.0055 | Irg 819 | 14 | 48.3 | 48 |
|  | Mono-AG | 24 | 36.2 | 48 |
|  | Bis-AG | 9 | 85.6 | 66 |
| 0.0014 | Irg 819 | 23 | 30.4 | 42 |
|  | Mono-AG | 52 | 16.4 | 30 |
|  | Bis-AG | 12 | 61.0 | 56 |

Example 8

Synthesis of 1,1-bis(2-phenyl-1,3-dithian-2-yl)germinane

Under an inert gas atmosphere 48.30 g (0.246 mol) 2-phenyl-1,3-dithian was dissolved in 300 ml absolute tetrahydrofuran and 98.4 ml (0.246 mol) n-butyllithium (in hexane~2.5 $moll^{-1}$) was added at 0° C. The mixture was stirred for 2 hrs at 0° C. and a solution of 24.3 g (0.114 mol) 1,1-dichlorogerminane (content~70-90%) in 50 ml absolute tetrahydrofuran was added dropwise. To complete the reaction the reaction mixture was first stirred for a further 2 hrs at 0° C. and then left to stand over night at 4° C. The reaction mixture was quenched with 30 ml water (strong brightening to weak-yellow solution), the organic phase diluted with 250 ml ethyl acetate and washed with 2×50 ml water each time. The purified aqueous phases were reextracted with 2×100 ml ethyl acetate each time. The purified organic phases were washed with saturated common salt solution, dried over sodium sulphate and reduced. After drying in a fine vacuum 51 g of a light-yellow greasy solid was obtained, which was stirred up for 1 hr. with 30 ml ethyl acetate. The deposit was sucked out and dried at 50° C. in a vacuum. 27.35 g (45%) of a white solid with MP: 159-160° C. was obtained.

$^1$H-NMR (400 MHz; $CDCl_3$): 1.19-1.23 (m, 2H, C$\underline{H}_2$—$C_2H_4$—Ge), 1.36-1.42 (m, 4H, C$\underline{H}_2$—$CH_2$—Ge), 1.48-1.55 (m, 4H, $CH_2$—Ge), 1.76-1.82 and 1.93-2.03 (m, 2×2H, C$\underline{H}_2CH_2$S), 2.27-2.32 and 2.70-2.77 (m, 2×4H, $CH_2$S), 7.12-7.17 (m, 2H, Ar—$H^4$), 7.25-7.31 (m, 4H, Ar—$H^{2,6}$), 7.90-7.93 (m, 4H, Ar—$H^{3,5}$) $^{13}$C-NMR (100 MHz; $CDCl_3$): 11.45 ($CH_2$—Ge), 25.4, 26.0, 26.2, 26.6, and 28.5 ($CH_2CH_2$), 51.2 (S—C—S), 128.2, 129.0 and 133.6 (Ar—$C^{2-6}$), 140.7 (Ar—$C^1$)

Example 9

Synthesis of 1,1-bisbenzoyl-germinane

In a dry 500 ml round-bottomed flask 16.91 g (31.7 mmol) 1,1-bis(2-phenyl-1,3-dithian-2-yl)-germinane was dissolved in 300 ml tetrahydrofuran and 50 ml water under yellow light (whole reaction including purification). After adding 16.68 g (0.167 mol) calcium carbonate the suspension was stirred for 5 min at room temperature and then reacted with 32.18 g (0.127 mol) iodine, wherein the reaction mixture foamed slightly and the temperature rose to approx. 30° C. Further stirring took place and after 1 or 2 hrs 16.68 g (0.167 mol) calcium carbonate and (at intervals of 5 min) 32.18 g (0.127 mol) iodine were added each time. As described, after 6 hrs and 24 hrs stirring a further 15 g (0.15 mol) calcium carbonate and 30 g (0.118 mol) iodine were added each time. After a total of 28 hrs 280 ml saturated aqueous sodium dithionite solution was carefully added to the reddish-brown reaction mixture (strong foaming) until the colour changed to yellow. The mixture was filtered via a sintered-glass filter and the filtration residue was washed with 6×100 ml ethyl acetate. The organic phase was washed with 2×100 ml water and the purified aqueous phases reextracted with 2×100 ml ethyl acetate each time. The purified organic phases were dried over sodium sulphate, filtered and reduced at the rotary evaporator. 100 ml dichloromethane was added to the residue and the reaction mixture filtered via a frit filled with silica gel (silica gel 60, 0.035-0.070 mm, 40 g, diameter 50 mm; approx. 600 ml dichloromethane). The eluate was reduced at the rotary evaporator and dried in the fine vacuum. 10.95 g (31.0 mmol; 98%) of a waxy yellow raw product was obtained which was purified by column chromatography (silica gel 60, 0.035-0.070 mm, n-hexane/ethyl acetate 20:1; $R_f$=0.3). 7.33 g (20.8 mmol; 66%) of a yellow solid with a melting point of 85-88° C. was obtained.

$^1$H-NMR (400 MHz; $CDCl_3$): 1.41-1.47 (m, 2H, C$\underline{H}_2$—$C_2H_4$—Ge), 1.60-1.63 (m, 4H, C$\underline{H}_2$—$CH_2$—Ge), 1.78-1.84 (m, 4H, $CH_2$—Ge), 7.40-7.51 (m, 6H, Ar—$H^{3,4,5}$), 7.75-7.78 m, 4H, Ar—$H^{2,6}$) $^{13}$C-NMR (100 MHz; $CDCl_3$): 14.4 ($CH_2$—Ge), 25.6 and 29.1 ($CH_2CH_2$), 128.2, 129.0 and 133.6 (Ar—$C^{2-6}$), 140.7 (Ar—$C^1$), 229.0 (C=O)

The absorption maximum of the Norrish type I photoinitiator 1,1-bisbenzoyl-germinane is 418.1 nm.

Example 10

Preparation of a Composite Cement Using the bisbenzoyidiethylgermanium from Example 3 or the 1,1-bisbenzoyl-germinane from Example 9

In accordance with Table 10 below, analogously to Example 4, composite fixing cements based on a methacrylate mixture and incorporating either two different concentrations of bisbenzoyldiethylgermanium from Example 3 (cement A to B) or of 1,1-bisbenzoylgerminane from Example 9 (cements C and D) were prepared. The cements A and C or B and D contained the same molar concentration of photoinitiator. In analogous manner to Example 6 test pieces were prepared from the materials, cured, and the bending strength and the bending E modulus determined. The results are shown in Table 11.

TABLE 10

Composition of the composite cements (details in wt.-%)

| Component | Cement A | Cement B | Cement C | Cement D |
|---|---|---|---|---|
| Bisbenzoyldiethylgermanium | 0.16 | 0.49 | — | — |
| 1,1-bisbenzoyl-germinane | — | — | 0.21 | 0.64 |
| UDMA[1] | 32.06 | 31.72 | 32.01 | 31.56 |

TABLE 10-continued

Composition of the composite cements
(details in wt.-%)

| Component | Cement A | Cement B | Cement C | Cement D |
|---|---|---|---|---|
| Triethyleneglycol dimethacrylate | 7.80 | 7.82 | 7.81 | 7.81 |
| Aerosil OX-50 (Degussa) | 41.27 | 41.27 | 41.26 | 41.27 |
| Ytterbium trifluoride (Rhone-Poulenc) | 18.71 | 18.70 | 18.71 | 18.72 |

[1] Addition product of 2 mol 2-hydroxyethylmethacrylate and 1 mol 2,2,4-trimethylhexamethylene diisocyanate

TABLE 11

Properties of the composite cements

| Component | Cement A | Cement B | Cement C | Cement D |
|---|---|---|---|---|
| Bending strength (MPa) after 24 h WI[1] | 119 | 143 | 124 | 133 |
| Elastic modulus (MPa) after 24 h WI[1] | 5615 | 6345 | 5439 | 6101 |

[1] WI = water immersion of the test pieces at 37° C.

Example 11

Preparation of a Cationically Polymerizable Composite Using the Bisbenzoyldiethylgermanium from Example 3

In accordance with Table 12 below, analogously to Example 5, a composite based on the commercial cycloaliphatic oligo(dimethylsiloxane)diepoxide Silbione UV Polymer 30 and a mixture of the cationic photoinitiator Rhodorsil 2074 (isopropylphenyl-methylphenyl-iodoniumtetrakis(pentafluorophenyl borate, Rhodia) and bisbenzoyldiethylgermanium from Example 3 was prepared. Analogously to Example 5, test pieces were prepared from the materials, cured, and the bending strength and the bending E modulus determined. The results are shown in Table 13.

TABLE 12

Composition of the cationic filler composite
(details in wt.-%)

| Component | Composite |
|---|---|
| Monomer resin[1] | 25.4 |
| Glass filler G018-163 (Schott)[2] | 63.9 |
| Ytterbiumtrifluoride (Rhone-Poulenc) | 10.4 |
| OX-50[3] | 0.3 |

[1] Mixture of 96.8 wt.-% Silbione UV Polymer 30, 3.0 wt.-% Rhodorsil 2074 and 0.2 wt.-% bisbenzoyldiethylgermanium
[2] Silanized Sr—Al-boron silicate glass filler with an average particle size of 1.0 μm,
[3] Silanized pyrogenic SiO$_2$ OX-50 (Degussa).

TABLE 13

Properties of the cationic composite

| | Cationic composite |
|---|---|
| Bending strength (MPa) after 24 h WI[1] | 90 |
| Elastic modulus (MPa) after 24 h WI[1] | 8700 |

[1] WI = water immersion of the test pieces at 37° C.

Example 12

Preparation of a Coating Using the Bisbenzoyidiethylgermanium from Example 3

In accordance with Table 14 below, a coating material based on a mixture of methyl methacrylate (MMA), pentaerythritol tetraacrylate (SR-295) methacrylate mixture and the triacrylate V-546 was prepared using the bisbenzoyldiethylgermanium from Example 3 (coating A) or a mixture of camphorquinone (CC) and 4-(N,N-dimethylamino)benzoic acid diethyl ester (EMBO) (comparison coating B).

TABLE 14

Composition of two coating materials
(details in wt.-%)

| Component | Coating A | Coating B |
|---|---|---|
| MMA | 27.8 | 28.1 |
| SR-295 | 20.833 | 20.0 |
| V-546[1] | 51.133 | 50.0 |
| Bisbenzoyldiethylgermanium | 0.034 | — |
| CC | — | 0.35 |
| EMBO | — | 0.55 |

[1] HPA adduct of 3 mol hydroxypropylacrylate to 1 mol of asymmetric trimer of hexamethylene diisocyanate The coating materials were applied in each case with a microbrush to a composite test piece (Systemp. C&B plus, Ivoclar Vivadent AG) and irradiated for 20 with an Astralis 7 halogen lamp (Ivoclar Vivadent AG) or LED Bluephase (Ivoclar Vivadent AG). A colourless non-sticky surface resulted with coating A, while the surface with the comparison coating was light yellow and sticky.

All numbers expressing quantities or parameters used in the specification are to be understood as additionally being modified in all instances by the term "about". Notwithstanding that the numerical ranges and parameters set forth the broad scope of the subject matter presented herein are approximations, the numerical values set forth are indicated as precisely as possible. For example, any numerical value may inherently contains certain errors resulting from the standard deviation reflected by inaccuracies in their respective measurement techniques, or round-off errors and inaccuracies.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

We claim:

1. A composition with at least one polymerizable binder and at least one polymerization initiator, the composition comprising at least one acylgermanium compound according to Formula (I), Formula (I)

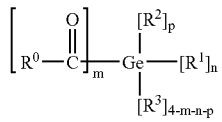

in which
R⁰ is C$_{1-18}$ alkyl, C$_{2-18}$ alkenyl, wherein these radicals can be unsubstituted or substituted one or more times by halogen, —OR$^{10}$, —OCO—R$^{10}$, —OCO-hal, —COO—R$^{10}$, —CH═CH—CO—OR$^{10}$, —N(R$^{11}$)—CO—R$^{10}$, —N(R$^{11}$)—CO-hal, —C(C$_{1-4}$-alkyl)═C(C$_{1-4}$-alkyl)-CO—OR$^{10}$, —CO—NR$^{11}$R$^{12}$, —CH═CH-phenyl, —C(C$_{1-4}$-alkyl)═C(C$_{1-4}$-alkyl) phenyl, C$_{3-12}$ cycloalkyl, C$_{2-18}$ alkenyl, phenyl-C$_{1-4}$-alkyl, phenyl, naphthyl, antryl, biphenyl, a saturated or unsaturated 5 or 6-membered O, S or N-containing heterocyclic ring, wherein said ring systems can be unsubstituted or substituted by 1 to 5 halogen atoms, C$_{1-8}$ alkyl, C$_{1-8}$ alkoxy and/or C$_{1-8}$ alkylthio radicals, or R⁰ comprises:

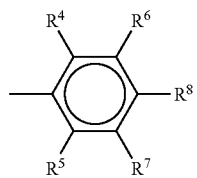

wherein
R⁴, R⁵ independently of each are H, halogen, a branched or linear C$_{1-6}$ alkyl or —O—C$_{1-6}$-alkyl radical which can be interrupted by one or more oxygen atoms;
R⁶, R⁷, R⁸ independently of each other are H, halogen, a branched, cyclic or linear C$_{1-20}$ alkyl, -alkenyl, -alkyloxy or -alkenoxy radical, which can be interrupted by one or more O, S or —NR'— and can be substituted by one or more polymerizable groups and/or radicals R⁹, wherein R' is H, halogen, a branched, cyclic or linear C$_{1-20}$ alkyl, -alkenyl, -alkyloxy or -alkenoxy radical;
wherein
R⁹ is —OH, —C$_x$F$_{2x+1}$ with x=1 to 20, —[Si(CH$_3$)$_2$]$_y$—CH$_3$ with y=1 to 20;
R$^{10}$ is H; C$_{1-18}$ alkyl, C$_{1-18}$ alkyl which is interrupted by one or more oxygen atoms; C$_{2-18}$ alkenyl; C$_{2-18}$ alkenyl which is interrupted by one or more oxygen atoms; C$_{3-12}$ cycloalkyl; tetrahydropyran-2-yl, phenyl-C$_{1-20}$-alkylene; phenyl-C$_{1-20}$-alkenylene, C$_{1-6}$ alkyl which can be unsubstituted or substituted by halogen, cyclohexyl, cyclopentyl, tetrahydrofuranyl, furanyl or isopropyl-4-methyl-cyclohexyl, phenyl, naphthyl or biphenyl, wherein these ring systems can be unsubstituted or substituted by 1 to 5 halogen atoms, C$_{1-8}$-alkyl, C$_{1-8}$-alkoxy and/or C$_{1-8}$-alkylthio radicals,
R$^{11}$, R$^{12}$ independently of each other are H; C$_{1-18}$ alkyl, C$_{1-18}$ alkyl which is interrupted by one or more oxygen atoms; C$_{2-18}$ alkenyl, C$_{2-18}$ alkenyl which is interrupted by one or more oxygen atoms; C$_{3-12}$ cycloalkyl, phenyl-C$_{1-4}$-alkyl, phenyl, naphthyl or pyridyl, wherein these ring systems can be unsubstituted or substituted by 1 to 5 halogen atoms, C$_{1-8}$-alkyl, C$_{1-8}$-alkoxy and/or C$_{1-8}$-alkylthio radicals, or R$^{11}$ and R$^{12}$ together form a 5 or 6-membered O, S or N-containing heterocyclic ring which for its part can be anellated with an aliphatic or aromatic ring,
R¹, R² independently of each other are:

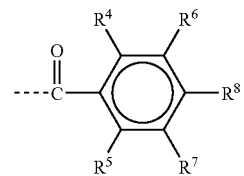

or H, or have one of the meanings given for R³;
wherein
R⁴, R⁵ independently of each other are H, halogen, a branched or linear C$_{1-6}$ alkyl or —O—C$_{1-6}$-alkyl radical which can be interrupted by one or more oxygen atoms;
R⁶, R⁷, R⁸ independently of each other are H, halogen, a branched, cyclic or linear C$_{1-20}$ alkyl, -alkenyl, -alkyloxy or -alkenoxy radical, which can be interrupted by one or more O, S or —NR'— and can be substituted by one or more polymerizable groups and/or radicals R⁹, wherein R' is H, halogen, a branched, cyclic or preferably linear C$_{1-20}$ alkyl, -alkenyl, -alkyloxy or -alkenoxy radical;
wherein R⁹ is defined as above;

and
R³ is a branched or linear C$_{1-18}$ alkyl radical or C$_{2-18}$ alkenyl radical, wherein these radicals can be unsubstituted or substituted one or more times by a radical which is selected from the following group:
halogen, CN,

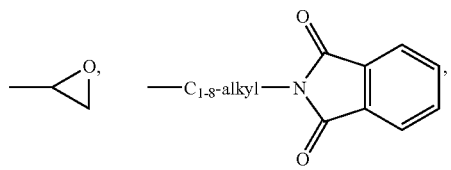

—OR$^{10}$, —SR$^{10}$, —OCO—R$^{10}$, —COO—R$^{10}$, —CH═CH—CO—OR$^{10}$, —C(C$_{1-4}$-alkyl)═C(C$_{1-4}$-alkyl)-CO—OR$^{10}$, —CO—R$^{13}$, —CO—CH═CH—CO—C$_{1-6}$-alkyl, —CO—CH═CH—CO-phenyl, —CO—CH═CH—COO—C$_{1-18}$-alkyl, —NR$^{11}$R$^{12}$, —N(R$^{11}$)—CO—R$^{10}$, —N(R$^{11}$)—COO—R$^{10}$, —N(R$^{11}$)—CO—NR$^{11}$R$^{12}$, —N(R$^{11}$)—CO-hal, —CO—NR$^{11}$R$^{12}$—SO$_2$—R$^{10}$, —SO$_2$—OR$^{10}$, —SO$_2$—NR$^{11}$R$^{12}$, —PO(OC$_{1-8}$-alkyl)$_2$, —SiR$^{14}$R$^{15}$R$^{16}$, —CH═CH-phenyl, —C(C$_{1-4}$-alkyl)═C(C$_{1-4}$ alkyl)phenyl, phenyl-C$_{1-4}$-alkyl, phenyl, naphthyl, biphenyl, C$_{5-12}$-cycloalkyl, a saturated or unsaturated 5 or 6-membered O, S or N-containing heterocyclic ring, benzophenonyl, thisanthonyl,
wherein
R$^{10}$, R$^{11}$ and R$^{12}$ are as defined above;
wherein
R$^{13}$ is C$_{1-18}$ alkyl, C$_{2-18}$ alkenyl which is interrupted by one or more O atoms, C$_{3-12}$ cycloalkyl, phenyl- $C_{1-4}$-alkyl, phenyl, naphthyl or biphenyl, wherein these ring systems can be unsubstituted or substituted by 1 to 5 $C_{1-8}$ alkyl, $C_{1-8}$ alkoxy, $C_{1-8}$ alkylthio radicals and/or halogen atoms;

$R^{14}$, $R^{15}$, $R^{16}$ independently of each other are H, $C_{1-8}$ alkyl, $C_{2-8}$ alkenyl, $C_{7-9}$ phenylalkyl, —O—$C_{1-8}$-alkyl, phenyl or —O—$SiR^{17}R^{18}R^{19}$, wherein $R^{17}$, $R^{18}$, $R^{19}$ independently of each other are H, $C_{1-8}$ alkyl, $C_{2-8}$ alkenyl, $C_{7-9}$ phenylalkyl, —O—$C_{1-8}$-alkyl or phenyl, or $R^3$ is a branched or linear $C_{2-18}$ alkyl radical or a $C_{2-18}$ alkylene radical which is interrupted one or more times by —O—, —NH—, —$NR^{11}$—, —S—, wherein the radicals can be unsubstituted or substituted one or more times by a radical which is chosen from the following group:

halogen, CN, —$OR^{10}$, —$SR^{10}$, —OCO—$R^{10}$, —COO—$R^{10}$, —$NR^{11}R^{12}$—$N(R^{11})$—CO—$R^{10}$, —$N(R^{11})$—COO—$R^{10}$, —$N(R^{11})$—CO—$NR^{11}R^{12}$, —$N(R^{11})$—CO-hal, —CO—$NR^{11}R^{12}$, —$SO_2$—$R^{10}$, —$SO_2$—$OR^{10}$, —$SO_2$—$NR^{11}R^{12}$, —PO(O$C_{1-8}$-alkyl)$_2$, —$SiR^{14}R^{15}R^{16}$, phenyl-$C_{1-4}$-alkyl, phenyl, $C_{5-12}$ cycloalkyl;

wherein $R^{10}$, $R^{11}$, $R^{12}$, $R^{14}$, $R^{15}$ and $R^{16}$ are as defined above;

or $R^3$ is a branched or linear $C_{2-18}$ alkyl radical or a $C_{2-18}$ alkylene radical which is interrupted one or more times by —CO—, —COO—, —OCO—, —OCOO—, —CO—$N(R^{12})$—, —$N(R^{12})$—CO—, —$N(R^{12})$—CO—$N(R^{12})$—, —$N(R^{12})$—COO—, —COO—$C_{1-6}$-alkylene, —COS—$C_{1-18}$-alkylene, —$SO_2$—, —$SO_2$—O—, —$SO_2$—$N(R^{12})$—, —$(CH_3)_2Si[OSi(CH_3)_2]_q$—, with q=1 to 6; phenyl-$C_{1-4}$-alkylene, phenylene, naphthylene, biphenylene, $C_{5-12}$ cycloalkylene or a 5 or 6-membered O, S or N-containing heterocyclic ring; wherein $R^{12}$ is as defined above;

or $R^3$ is trimethylsilyl, hal-$(CH_3)_2Si$—$[OSi(CH_3)_2]_r$—, $(CH_3)_3Si$—$[OSi(CH_3)_2]_r$— with r=1 to 6, —COOH, —COO—$R^{10}$, —CO—$NR^{11}R^{12}$, —CO-vinyl, —CO-phenyl, wherein the phenyl radical can be unsubstituted or substituted by —$CH_3$, —$OCH_3$ and/or —Cl;

wherein $R^{10}$, $R^{11}$ and $R^{12}$ are as defined above;

or $R^3$ is phenyl-$C_{1-20}$-alkyl, phenyl, naphthyl or biphenyl, $C_{5-12}$ cycloalkyl or a saturated or unsaturated 5 or 6-membered O, S or N-containing heterocyclic ring, wherein these ring systems can be unsubstituted or substituted by 1 to 5 halogen atoms, $C_{1-8}$ alkyl, $C_{1-8}$ alkoxy, $C_{1-8}$ alkylthio radicals and/or —$NR^{11}R^{12}$, wherein $R^{11}$ and $R^{12}$ are as defined above;

or $R^3$ is halogen, OH, an aromatic $C_{6-30}$ radical which can be substituted by a branched, cyclic or linear $C_{1-20}$ alkyl, -alkenyl, -alkoxy or -alkenoxy radical, wherein the radicals can be interrupted by one or more O, S or N atoms and/or can be substituted by one or more polymerizable groups and/or radicals $R^9$, or is a branched, cyclic or linear $C_{1-20}$-alkyl, -alkenyl, -alkoxy or -alkenoxy radical which can be interrupted one or more times by O, S or —$NR^{20}$— and substituted by one or more polymerizable groups and/or radicals $R^9$, wherein $R^9$ is —OH, —$C_xF_{2x+1}$ with x=1 to 20, —$[Si(CH_3)_2]_y$—$CH_3$ with y=1 to 20, and $R^{20}$ is H, halogen, a branched, cyclic or linear $C_{1-20}$-alkyl, -alkenyl, -alkyloxy or -alkenoxy radical; and m is 1, 2 or 3, n is 0 or 1, p is 0 or 1, wherein two of the radicals $R^0$, $R^1$, $R^2$ or $R^3$ can be connected to each other to form a 5 to 8-membered ring, wherein the ring or rings can be anellated with one or more aliphatic or aromatic rings, unsubstituted or substituted one or more times and can contain further heteroatoms.

2. The composition according to claim 1, wherein $R^0$ is $C_{1-18}$ alkyl, $C_{2-18}$ alkenyl, wherein these radicals can be unsubstituted or substituted one or more times by halogen, —$OR^{10}$, —OCO—$R^{10}$, —OCO-hal, —COO—$R^{10}$, —CH=CH—CO—$OR^{10}$, —$N(R^{11})$—CO—$R^{10}$, —$N(R^{11})$—CO-hal, —$C(C_{1-4}$-alkyl)=$C(C_{1-4}$-alkyl)-CO—$OR^{10}$, —CO—$NR^{11}R^{12}$—CH=CH-phenyl, —$C(C_{1-4}$-alkyl)=$C(C_{1-4}$-alkyl) phenyl, $C_{3-12}$ cycloalkyl, $C_{2-18}$ alkenyl, phenyl-$C_{1-4}$-alkyl, phenyl, naphthyl, antryl, biphenyl, a 5 or 6-membered O, S or N-containing heterocyclic ring, wherein all named ring systems can be unsubstituted or substituted by 1 to 5 halogen atoms, $C_{1-8}$ alkyl, $C_{1-8}$ alkoxy and/or $C_{1-8}$ alkylthio radicals, or

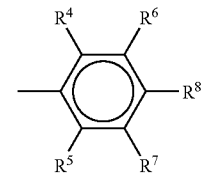

wherein $R^{10}$ is H, $C_{1-18}$ alkyl, $C_{2-18}$ alkenyl, $C_{2-18}$ alkenyl which is interrupted by one or more oxygen atoms, $C_{3-12}$ cycloalkyl, tetrahydropyran-2-yl, phenyl-$C_{1-4}$-alkylene, phenyl-$C_{1-4}$-alkenylene, $C_{1-6}$ alkyl, which can be unsubstituted or substituted by halogen, cyclohexyl, cyclopentyl, tetrahydrofuranyl, furanyl or isopropyl-4-methyl-cyclohexyl, is phenyl, naphthyl or biphenyl, wherein these ring systems can be unsubstituted or substituted by 1 to 5 halogen atoms, $C_{1-8}$ alkyl, $C_{1-8}$ alkoxy and/or $C_{1-8}$ alkylthio radicals, $R^{11}$, $R^{12}$ independently of each other are H, $C_{1-18}$ alkyl, $C_{2-18}$ alkenyl, $C_{2-18}$ alkenyl which is interrupted by one or more oxygen atoms, $C_{3-12}$ cycloalkyl, phenyl-$C_{1-4}$-alkyl, phenyl, naphthyl or pyridyl, wherein these ring systems can be unsubstituted or substituted by 1 to 5 halogen atoms, $C_{1-8}$ alkyl, $C_{1-8}$ alkoxy and/or $C_{1-8}$ alkylthio radicals, or $R^{11}$ and $R^{12}$ together form a 5 or 6-membered O, S or N-containing heterocyclic ring which for its part can be anellated with an aliphatic or aromatic ring, $R^1$, $R^2$ independently of each other are

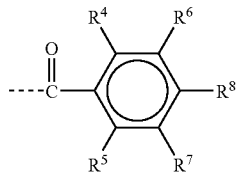

or H, or have one of the meanings given for $R^3$;
wherein
$R^4$, $R^5$ independently of each other are in each case H, halogen, a linear or branched $C_{1-6}$-alkyl or —O—$C_{1-6}$-alkyl radical;
$R^6$, $R^7$, $R^8$ independently of each other are in each case H, halogen, a branched, cyclic or linear $C_{1-20}$-alkyl, -alkenyl, -alkyloxy or -alkenoxy radical which can be interrupted by one or more O, S or —$NR^{20}$— and can be substituted by one or more polymerizable groups and/or radicals $R^9$,
wherein
$R^9$ is —OH, —$C_xF_{2x+1}$ with x=1 to 20, —$[Si(CH_3)_2]_y$—$CH_3$ with y=1 to 20; and
$R^{20}$ is H, halogen, a branched, cyclic or preferably linear $C_{1-20}$ alkyl, -alkenyl, -alkyloxy or -alkenoxy radical;
$R^3$ is a branched or linear $C_{1-18}$ alkyl radical or $C_{2-18}$ alkenyl radical, wherein these radicals can be unsubstituted or substituted one or more times by a radical which is selected from the following group:
halogen, CN,

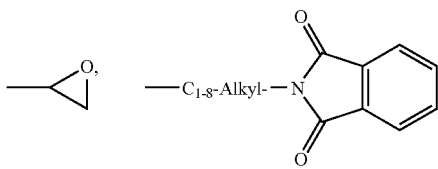

—$OR^{10}$, —$SR^{10}$, —OCO—$R^{10}$, —COO—$R^{10}$, —CH=CH—CO—$OR^{10}$, —C($C_{1-4}$-alkyl)=C($C_{1-4}$-alkyl)-CO—$OR^{10}$, —CO—$R^{13}$, —CO—CH=CH—CO—$C_{1-6}$ alkyl, —CO—CH=CH—CO phenyl, —CO—CH=CH—COO—$C_{1-18}$ alkyl, —$NR^{11}R^{12}$, —$N(R^{11})$—CO—$R^{10}$, —$N(R^{11})$—COO—$R^{10}$, —$N(R^{11})$—CO—$NR^{11}R^{12}$, —$N(R^{11})$—CO-hal, —CO—$NR^{11}R^{12}$, —$SO_2$—$R^{10}$, —$SO_2$—$OR^{10}$, —$SO_2$—$NR^{11}R^{12}$, —$PO(OC_{1-8}$-alkyl$)_2$, —$SiR^{14}R^{15}R^{16}$, —CH=CH-phenyl, —C($C_{1-4}$-alkyl)=C($C_{1-4}$ alkyl)phenyl, phenyl-$C_{1-4}$-alkyl, phenyl, naphthyl, biphenyl, $C_{5-12}$ cycloalkyl, a 5 or 6-membered O, S or N-containing heterocyclic ring, benzophenonyl, thisanthonyl,
wherein $R^{10}$, $R^{11}$ and $R^{12}$ are as defined above;
wherein
$R^{13}$ is $C_{1-18}$ alkyl, $C_{2-18}$ alkenyl which is interrupted by one or more O atoms, $C_{3-12}$ cycloalkyl, phenyl-$C_{1-4}$-alkyl, phenyl, naphthyl or biphenyl, wherein the named ring systems can be unsubstituted or substituted by 1 to 5 $C_{1-8}$ alkyl, $C_{1-8}$ alkoxy, $C_{1-8}$ alkylthio radicals and/or halogen atoms;

$R^{14}$, $R^{15}$, $R^{16}$ independently of each other are H, $C_{1-8}$ alkyl, $C_{2-8}$ alkenyl, $C_{7-9}$ phenylalkyl, —O—$C_{1-8}$ alkyl, phenyl or —O—$SiR^{17}R^{18}R^{19}$,
wherein
$R^{17}$, $R^{18}$, $R^{19}$ independently of each other are H, $C_{1-8}$ alkyl, $C_{2-8}$ alkenyl, $C_{7-9}$ phenylalkyl, —O—$C_{1-8}$ alkyl or phenyl,
or
$R^3$ is a branched or linear $C_{2-18}$ alkyl radical or a $C_{2-18}$ alkylene radical which is interrupted one or more times by —O—, —NH—, —$NR^{11}$—, —S—, wherein the radicals can be unsubstituted or substituted one or more times by a radical which is chosen from the following group:
halogen, CN, —$OR^{10}$, —$SR^{10}$, —OCO—$R^{10}$, —COO—$R^{10}$, —$NR^{11}R^{12}$—$N(R^{11})$—CO—$R^{10}$, —$N(R^{11})$—COO—$R^{10}$, —$N(R^{11})$—CO—$NR^{11}R^{12}$, —$N(R^{11})$—CO-hal, —CO—$NR^{11}R^{12}$, —$SO_2$—$R^{10}$, —$SO_2$—$OR^{10}$, —$SO_2$—$NR^{11}R^{12}$, —$PO(OC_{1-8}$-alkyl$)_2$, —$SiR^{14}R^{15}R^{16}$, phenyl-$C_{1-4}$-alkyl, phenyl, $C_{5-12}$ cycloalkyl;
wherein $R^{10}$, $R^{11}$ and $R^{12}$ are as defined above;
or
$R^3$ is a branched or linear $C_{2-18}$ alkyl radical or a $C_{2-18}$ alkylene radical which is interrupted one or more times by —CO—, —COO—, —OCO—, —OCOO—, —CO—$N(R^{11})$—, —$N(R^{11})$—CO—, —$N(R^{11})$—CO—$N(R^{11})$—, —$N(R^{11})$—COO—, —COO—$C_{1-6}$-alkylene, —COS—$C_{1-18}$-alkylene, —$SO_2$—, —$SO_2$—O—, —$SO_2$—$N(R^{11})$—, —$(CH_3)_2Si[OSi(CH_3)_2]_q$—, with q=1 to 6; phenyl-$C_{1-4}$-alkylene, phenylene, naphthylene, biphenylene, $C_{5-12}$ cycloalkylene or a 5 or 6-membered O, S or N-containing heterocyclic ring;
wherein $R^{11}$ is as defined above;
or
$R^3$ is trimethylsilyl, hal-$(CH_3)_2Si$—$[OSi(CH_3)_2]_r$—, $(CH_3)_3Si$—$[OSi(CH_3)_2]_r$— with r=1 to 6, —COOH, —COO—$R^{10}$, —CO—$NR^{11}R^{12}$, —CO-vinyl, —CO-phenyl, wherein the phenyl radical can be unsubstituted or substituted by —$CH_3$, —$OCH_3$ and/or —Cl;
wherein $R^{10}$, $R^{11}$ and $R^{12}$ are as defined above;
or
$R^3$ is phenyl-$C_{1-4}$-alkyl, phenyl, naphthyl or biphenyl, $C_{5-12}$ cycloalkyl or a 5 or 6-membered O, S or N-containing heterocyclic ring, wherein these ring systems can be unsubstituted or substituted by 1 to 5 halogen atoms, $C_{1-8}$ alkyl, $C_{1-8}$ alkoxy, $C_{1-8}$ alkylthio radicals and/or —$NR^{11}R^{12}$,
wherein $R^{11}$ and $R^{12}$ are as defined above;
or
$R^3$ is halogen, OH, an aromatic $C_{6-30}$ radical which can be substituted by a branched, cyclic or linear $C_{1-20}$ alkyl, -alkenyl, -alkoxy or -alkenoxy radical, wherein the named radicals can be interrupted one or more times by O, S or —$NR^{20}$— and/or can be substituted by one or more polymerizable groups and/or radicals $R^9$, or is a branched, cyclic or linear $C_{1-20}$ alkyl, -alkenyl, -alkoxy or -alkenoxy radical which can be interrupted one or more times by O, S or —$NR^{20}$— and substituted by one or more polymerizable groups and/or radicals $R^9$,
wherein $R^9$ and $R^{20}$ are as defined above and
m is 1, 2 or 3,
n is 0 or 1,
p is 0 or 1.

3. A composition with at least one polymerizable binder and at least one polymerization initiator, the composition comprising at least one acylgermanium compound according to Formula (II),

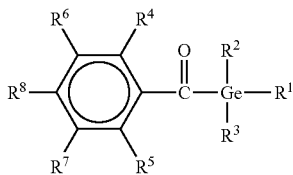

Formula (II)

in which
R$^1$, R$^2$ independently of each other are

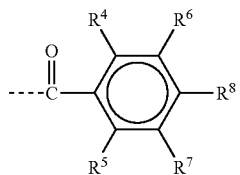

or H, or have one of the meanings given for R$^3$;

R$^3$ is halogen, OH, an aromatic C$_{6-30}$ radical which can be substituted by a branched, cyclic or linear C$_{1-20}$ alkyl, -alkenyl, -alkoxy or -alkenoxy radical, wherein the named radicals can be interrupted one or more times by O, S or —NR$^{20}$— and/or can be substituted by one or more polymerizable groups and/or radicals R$^9$, or is a branched, cyclic or preferably linear C$_{1-20}$ alkyl, -alkenyl, -alkoxy or -alkenoxy radical which can be interrupted one or more times by O, S or —NR$^{20}$— and can be substituted by one or more polymerizable groups and/or radicals R$^9$;

R$^4$, R$^5$ independently of each other are H, halogen, a linear or branched C$_{1-6}$ alkyl or —O—C$_{1-6}$ alkyl radical;

R$^6$, R$^7$, R$^8$ independently of each other are H, halogen, a branched, cyclic or linear C$_{1-20}$ alkyl, -alkenyl, -alkyloxy or -alkenoxy radical which is interrupted one or more times by O, S or —NR$^{20}$— and can be substituted by one or more polymerizable groups and/or radicals R$^9$;

R$^9$ is —OH, —C$_x$F$_{2x+1}$ with x=1 to 20, —[Si(CH$_3$)$_2$]$_y$—CH$_3$ with y=1 to 20; and R$^{20}$ is H, halogen, a branched, cyclic or linear C$_{1-20}$ alkyl, -alkenyl, -alkyloxy or -alkenoxy radical.

4. A composition with at least one polymerizable binder and at least one polymerization initiator, the composition comprising at least an acylgermanium compound according to Formula (III):

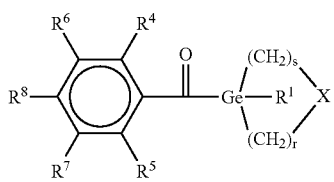

Formula (III)

in which
R$^1$ is

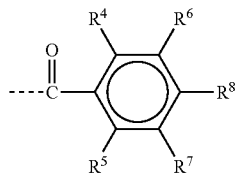

or H, or has one of the meanings given for R$^3$;

R$^3$ is a branched or linear C$_{1-18}$ alkyl radical or C$_{2-18}$ alkenyl radical, wherein these radicals can be unsubstituted or substituted one or more times by a radical which is selected from the following group:
halogen, CN,

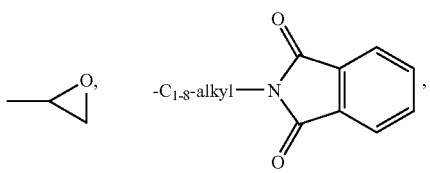

—OR$^{10}$, —SR$^{10}$, —OCO—R$^{10}$, —COO—R$^{10}$, —CH=CH—CO—OR$^{10}$, —C(C$_{1-4}$-alkyl)=C(C$_{1-4}$-alkyl)-CO—OR$^{10}$, —CO—R$^{13}$, —CO—CH=CH—CO—C$_{1-6}$alkyl, —CO—CH=CH—CO phenyl, —CO—CH=CH—COO—C$_{1-18}$-alkyl, —NR$^{11}$R$^{12}$, —N(R$^{11}$)—CO—R$^{10}$, —N(R$^{11}$)—COO—R$^{10}$, —N(R$^{11}$)—CO—NR$^{11}$R$^{12}$, —N(R$^{11}$)—CO-hal, —CO—NR$^{11}$R$^{12}$, —SO$_2$—R$^{10}$, —SO$_2$—OR$^{10}$, —SO$_2$—NR$^{11}$R$^{12}$, —PO(OC$_{1-8}$-alkyl)$_2$, —SiR$^{14}$R$^{15}$R$^{16}$, —CH=CH-phenyl, —C(C$_{1-4}$-alkyl)=C(C$_{1-4}$alkyl)phenyl, phenyl-C$_{1-4}$-alkyl, phenyl, naphthyl, biphenyl, C$_{5-12}$-cycloalkyl, a saturated or unsaturated 5 or 6-membered O, S or N-containing heterocyclic ring, benzophenonyl, thisanthonyl,
wherein
wherein R$^{10}$, R$^{11}$ and R$^{12}$ are as defined above;
wherein
R$^{13}$ is C$_{1-18}$ alkyl, C$_{2-18}$ alkenyl which is interrupted by one or more O atoms, C$_{3-12}$ cycloalkyl, phenyl-C$_{1-4}$-alkyl, phenyl, naphthyl or biphenyl, wherein the named ring systems can be unsubstituted or substituted by 1 to 5 C$_{1-8}$ alkyl, C$_{1-8}$ alkoxy, C$_{1-8}$ alkylthio radicals and/or halogen atoms;

R$^{14}$, R$^{15}$, R$^{16}$ independently of each other are H, C$_{1-8}$ alkyl, C$_{2-8}$ alkenyl, C$_{7-9}$ phenylalkyl, —O—C$_{1-8}$ alkyl, phenyl or —O—SiR$^{17}$R$^{18}$R$^{19}$,
wherein
R$^{17}$, R$^{18}$, R$^{19}$ independently of each other are H, C$_{1-8}$ alkyl, C$_{2-8}$ alkenyl, C$_{7-9}$ phenylalkyl, —O—C$_{1-8}$ alkyl or phenyl,
or
R$^3$ is a branched or linear C$_{2-18}$ alkyl radical or a C$_{2-18}$ alkylene radical which is interrupted one or more times by —O—, —NH—, —NR$^{11}$—, —S—, wherein the radicals can be unsubstituted or substituted one or more times by a radical which is chosen from the following group:

halogen, CN, —OR$^{10}$, —SR$^{10}$, —OCO—R$^{10}$, —COO—R$^{10}$, —NR$^{11}$R$^{12}$—N(R$^{11}$)—CO—R$^{10}$, —N(R$^{11}$)—COO—R$^{10}$, —N(R$^{11}$)—CO—NR$^{11}$R$^{12}$, —N(R$^{11}$)—CO-hal, —CO—NR$^{11}$R$^{12}$, —SO$_2$—R$^{10}$, —SO$_2$—OR$^{10}$, —SO$_2$—NR$^{11}$R$^{12}$, —PO(OC$_{1-8}$-alkyl)$_2$, —SiR$^{14}$R$^{15}$R$^{16}$, phenyl-C$_{1-4}$-alkyl, phenyl, C$_{5-12}$ cycloalkyl;

wherein R$^{10}$, R$^{11}$, R$^{12}$, R$^{14}$, R$^{15}$ and R$^{16}$ are as defined above;

or

R$^3$ is a branched or linear C$_{2-18}$ alkyl radical or a C$_{2-18}$ alkylene radical which is interrupted one or more times by —CO—, —COO—, —OCO—, —OCOO—, —CO—N(R$^{12}$)—, —N(R$^{12}$)—CO—, —N(R$^{12}$)—CO—N(R$^{12}$)—, —N(R$^{12}$)—COO—, —COO—C$_{1-6}$-alkylene, —COS—C$_{1-18}$-alkylene, —SO$_2$—, —SO$_2$—O—, —SO$_2$—N(R$^{12}$)—, —(CH$_3$)$_2$Si[OSi(CH$_3$)$_2$]$_q$—, with q=1 to 6; phenyl-C$_{1-4}$-alkylene, phenylene, naphthylene, biphenylene, C$_{5-12}$ cycloalkylene or a 5 or 6-membered O, S or N-containing heterocyclic ring; wherein R$^{12}$ is as defined above;

or

R$^3$ is trimethylsilyl, hal-(CH$_3$)$_2$Si—[OSi(CH$_3$)$_2$]$_r$—, (CH$_3$)$_3$Si—[OSi(CH$_3$)$_2$]$_r$— with r=1 to 6, —COOH, —COO—R$^{10}$, —CO—NR$^{11}$R$^{12}$, —CO-vinyl, —CO-phenyl, wherein the phenyl radical can be unsubstituted or substituted by —CH$_3$, —OCH$_3$ and/or —Cl;

wherein R$^{10}$, R$^{11}$ and R$^{12}$ are as defined above;

or

R$^3$ is phenyl-C$_{1-20}$-alkyl, phenyl, naphthyl or biphenyl, C$_{5-12}$ cycloalkyl or a saturated or unsaturated 5 or 6-membered O, S or N-containing heterocyclic ring, wherein these ring systems can be unsubstituted or substituted by 1 to 5 halogen atoms, C$_{1-8}$ alkyl, C$_{1-8}$ alkoxy, C$_{1-8}$ alkylthio radicals and/or —NR$^{11}$R$^{12}$, wherein R$^{11}$ and R$^{12}$ are as defined above or R$^3$ is halogen, OH, an aromatic C$_{6-30}$ radical which can be substituted by a branched, cyclic or linear C$_{1-20}$ alkyl, -alkenyl, -alkoxy or -alkenoxy radical, wherein the radicals can be interrupted one or more times by O, S or N and/or can be substituted by one or more polymerizable groups and/or radicals R$^9$, or is a branched, cyclic or linear C$_{1-20}$-alkyl, -alkenyl, -alkoxy or -alkenoxy radical which can be interrupted one or more times by O, S or —NR$^{20}$— and substituted by one or more polymerizable groups and/or radicals R$^9$, wherein R$^9$ is —OH, —C$_x$F$_{2x+1}$ with x=1 to 20, —[Si(CH$_3$)$_2$]$_y$—CH$_3$ with y=1 to 20; and R$^{20}$ is H, halogen, a branched, cyclic or linear C$_{1-20}$ alkyl, -alkenyl, -alkyloxy or -alkenoxy radical; and m is 1, 2 or 3, n is 0 or 1, p is 0 or 1, r, s independently of each other are an integer from 0 to 6, wherein r and s are chosen such that the sum of the ring atoms including the germanium atom is 5 to 8, and X is N—R$^{21}$, O, S or is absent, wherein R$^{21}$ is H or C$_{1-10}$ alkyl, and wherein the germanium-containing ring can be anellated with one or more aliphatic or aromatic rings and can be unsubstituted or substituted one or more times whereby the number of hydrogen atoms of the ring is correspondingly reduced.

5. The composition according to claim 1, wherein the polymerizable groups are selected from vinyl, styryl, (meth)acrylate, (meth)acrylamide or N-alkylacrylamide.

6. The composition according to claim 1, wherein the radicals R$^2$, R$^3$, R$^6$, R$^7$ and R$^8$ are substituted with 1 to 3 polymerizable groups.

7. The composition according to claim 1, comprising 0.001 to 5 weight % of the acylgermane of Formula (I).

8. The composition according to claim 1, wherein the polymerizable binder comprises at least one radically polymerizable monomer and/or prepolymer.

9. The composition according to claim 8, wherein the binder comprises a mono- or multifunctional (meth)acrylate, or a mixture thereof.

10. The composition according to claim 8, comprising at least one radically ring-opening polymerizable monomer.

11. The composition according to claim 1, wherein the binder comprises a mixture of mono- and/or multifunctional mercapto compounds and di- and/or multifunctional unsaturated monomers.

12. The composition according to claim 1, comprising at least one further initiator for radical polymerization.

13. The composition according to claim 1, comprising at least one further initiator for cationic polymerization.

14. The composition according to claim 1, further comprising a filler.

15. The composition according to claim 1, further comprising at least one additive which is selected from stabilizers, UV absorbers, slip additives, wetting agents, dispersants, adhesion promoters, matting and brightening agents, leveling agents and film-forming auxiliaries, antiskinning agents, light-protection agents, corrosion-protection agents, flame retardants, antioxidants, optical brighteners, flow improvers, thickeners and anti-foaming agents.

16. The composition of claim 1, comprising:
  0.001 to 5 weight % acylgermanium compound according to Formula (I),
  5 to 99.9 weight % polymerizable binder, and
  0 to 90 weight % filler.

17. The composition according to claim 16, comprising 0 to 50 weight % of a further additive.

18. A combination for the preparation of dental moldings, the combination comprising:
  the composition according to claim 1; and
  an LED light source.

19. The combination according to claim 18, wherein the LED light source has a wavelength in the range from 400 to 550 nm and the acylgermanium compound has an activation wavelength in the range from 400 to 550 nm.

20. A method for the preparation of a molding, comprising:
  molding the composition according to claim 1 into a body with the desired shape; and
  at least partially curing the body.

21. The method according to claim 20, comprising shaping the body so as to form one or more of: a dental crown, bridge, inlay or artificial tooth.

* * * * *